(12) United States Patent
Scheib et al.

(10) Patent No.: US 10,499,909 B2
(45) Date of Patent: Dec. 10, 2019

(54) APPARATUS AND METHOD FOR PLEATING A BODILY LUMEN

(71) Applicant: Ethicon Endo-Surgery, LLC, Guaynabo, PR (US)

(72) Inventors: Charles J. Scheib, Loveland, OH (US); Cortney E. Henderson, Loveland, OH (US); Tamara S. Vetro Widenhouse, Clarksville, OH (US); Edward G. Chekan, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 726 days.

(21) Appl. No.: 14/863,928

(22) Filed: Sep. 24, 2015

(65) Prior Publication Data

US 2017/0086822 A1   Mar. 30, 2017

(51) Int. Cl.
*A61B 17/072*  (2006.01)
*A61B 17/068*  (2006.01)
(Continued)

(52) U.S. Cl.
CPC ........ *A61B 17/068* (2013.01); *A61B 17/0482* (2013.01); *A61B 17/072* (2013.01); *A61B 17/07207* (2013.01); *A61B 17/07292* (2013.01); *A61B 17/105* (2013.01); *A61B 17/1155* (2013.01); *A61B 17/12009* (2013.01);
(Continued)

(58) Field of Classification Search
CPC ................ A61B 17/068; A61B 17/072; A61B 17/07207; A61B 17/07292; A61B 17/115; A61B 2017/07214; A61B 2017/00398; A61B 2017/2927

USPC .. 227/19, 175.1, 176.1, 175.2, 178.1, 180.1; 606/139, 153, 219
See application file for complete search history.

(56) References Cited

U.S. PATENT DOCUMENTS 4,805,823 A   2/1989 Rothfuss
5,205,459 A   4/1993 Brinkerhoff et al.
(Continued)

FOREIGN PATENT DOCUMENTS

EP   2 644 126 A2   10/2013
EP   2 764 824 A1   8/2014

OTHER PUBLICATIONS

European Search Report, Partial, dated Nov. 30, 2016 for Application No. EP 16190323.2, 6 pgs.
(Continued)

*Primary Examiner* — Scott A Smith
(74) *Attorney, Agent, or Firm* — Frost Brown Todd LLC

(57) ABSTRACT

An apparatus includes a staple cartridge. The staple cartridge includes staples, a deck, and a buttress. The deck defines a plurality of openings. Each opening of the plurality of openings is associated with a corresponding staple of the plurality of staples, such that each staple is configured to pass through a corresponding opening of the plurality of openings. The buttress is configured to detach from the staple deck in response to the staples being driven through the corresponding openings of the deck. The buttress is resiliently biased to transition from a first configuration while attached to the deck to a second configuration when detached from the deck. The buttress has a first length in the first configuration and a second length in the second configuration. The first length is longer than the second length.

17 Claims, 24 Drawing Sheets

(51) Int. Cl.
  *A61B 17/10* (2006.01)
  *A61B 17/32* (2006.01)
  *A61B 17/04* (2006.01)
  *A61B 17/115* (2006.01)
  *A61B 17/12* (2006.01)
  *A61B 17/00* (2006.01)
  *A61B 17/11* (2006.01)
  *A61B 17/29* (2006.01)

(52) U.S. Cl.
  CPC .... *A61B 17/32* (2013.01); *A61B 2017/00398* (2013.01); *A61B 2017/00818* (2013.01); *A61B 2017/00862* (2013.01); *A61B 2017/07214* (2013.01); *A61B 2017/1142* (2013.01); *A61B 2017/2927* (2013.01)

(56) References Cited

U.S. PATENT DOCUMENTS

| | | | |
|---|---|---|---|
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A | 9/1994 | Main et al. | |
| 5,397,324 A * | 3/1995 | Carroll | A61B 17/07207 128/898 |
| 5,415,334 A | 5/1995 | Williamson et al. | |
| 5,465,895 A | 11/1995 | Knodel et al. | |
| 5,533,661 A | 7/1996 | Main et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,702,409 A * | 12/1997 | Rayburn | A61B 17/07207 227/176.1 |
| 5,704,534 A | 1/1998 | Huitema et al. | |
| 5,752,965 A * | 5/1998 | Francis | A61B 17/07207 227/178.1 |
| 5,769,892 A * | 6/1998 | Kingwell | A61B 17/07207 227/178.1 |
| 5,810,855 A * | 9/1998 | Rayburn | A61B 17/07207 227/176.1 |
| 5,814,055 A | 9/1998 | Knodel et al. | |
| 5,814,057 A * | 9/1998 | Oi | A61B 17/072 227/178.1 |
| 5,902,312 A * | 5/1999 | Frater | A61B 17/07207 606/148 |
| 5,908,427 A * | 6/1999 | McKean | A61B 17/07207 606/139 |
| 6,099,551 A * | 8/2000 | Gabbay | A61B 17/07207 227/176.1 |
| 6,325,810 B1 * | 12/2001 | Hamilton | A61B 17/07207 227/175.1 |
| 6,592,597 B2 * | 7/2003 | Grant | A61B 17/072 227/175.1 |
| 6,638,285 B2 * | 10/2003 | Gabbay | A61B 17/072 606/139 |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 7,794,475 B2 | 9/2010 | Hess et al. | |
| 8,361,093 B2 | 1/2013 | Wright | |
| 8,408,439 B2 | 4/2013 | Huang et al. | |
| 8,453,914 B2 | 6/2013 | Laurent et al. | |
| 8,617,049 B2 | 12/2013 | Dlugos, Jr. et al. | |
| 8,910,847 B2 | 12/2014 | Nalagatla et al. | |
| 9,138,225 B2 | 9/2015 | Huang et al. | |
| 9,161,803 B2 | 10/2015 | Yates et al. | |
| 9,289,207 B2 | 3/2016 | Shelton, IV | |
| 9,463,022 B2 | 10/2016 | Swayze et al. | |
| 9,498,222 B2 | 11/2016 | Scheib et al. | |
| 9,597,082 B2 | 3/2017 | Stokes et al. | |
| 9,724,098 B2 | 8/2017 | Baxter, III et al. | |
| 2006/0004407 A1 * | 1/2006 | Hiles | A61B 17/072 606/215 |
| 2007/0246505 A1 * | 10/2007 | Pace-Floridia | A61B 17/07207 227/175.1 |
| 2009/0095791 A1 * | 4/2009 | Eskaros | A61B 17/072 227/175.1 |
| 2012/0289979 A1 * | 11/2012 | Eskaros | A61B 17/07292 606/151 |
| 2013/0256373 A1 * | 10/2013 | Schmid | A61B 17/07207 227/176.1 |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166717 A1 | 6/2014 | Swayze et al. | |
| 2014/0166728 A1 | 6/2014 | Swayze et al. | |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |
| 2016/0278774 A1 | 9/2016 | Shelton, IV et al. | |
| 2016/0374666 A1 | 12/2016 | DiNardo et al. | |
| 2016/0374670 A1 | 12/2016 | Fox et al. | |

OTHER PUBLICATIONS

European Search Report, Extended, and Written Opinion dated Mar. 3, 2017 for Application No. EP 16190323.2, 10 pgs.
International Search Report and Written Opinion dated Jan. 23, 2017 for Application No. PCT/US2016/052100, 16 pgs.

* cited by examiner

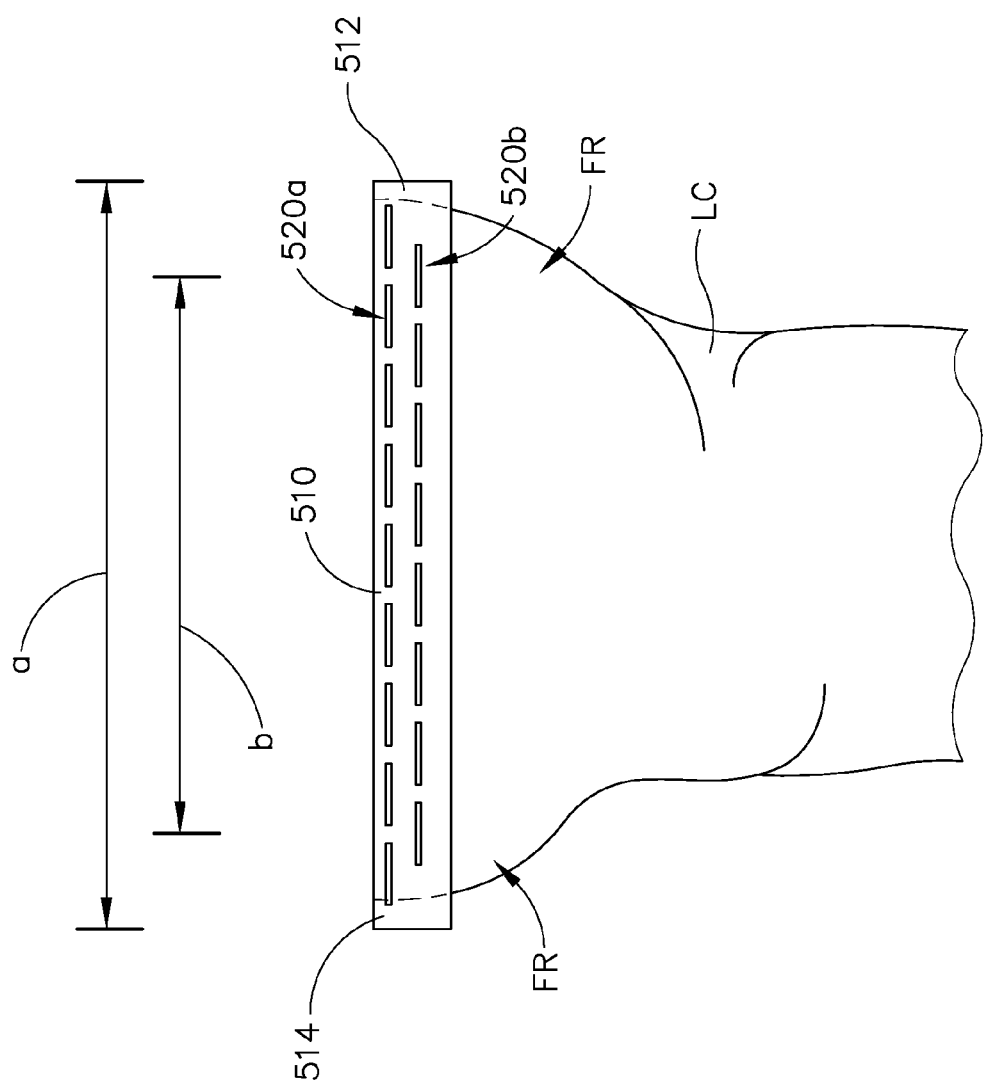

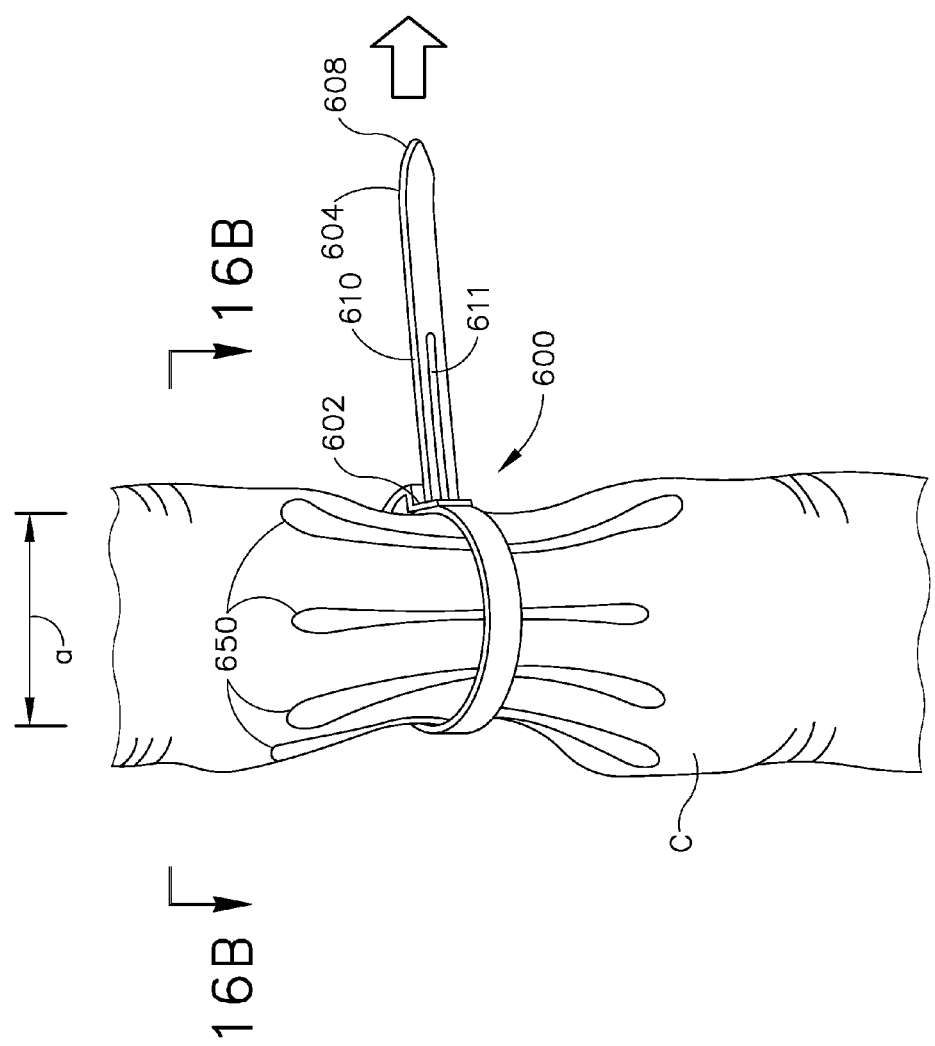

APPARATUS AND METHOD FOR PLEATING A BODILY LUMEN

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 12A depicts a side elevational view of portion of the gastrointestinal tract after having been stapled and severed utilizing the staple cartridge of FIG. 11, with the buttress in a stretched configuration;

FIG. 15C depicts a perspective view of the bendable pleating member of FIG. 14 cinched around the colon of the patient to form an array of pleats;

Figure 1:
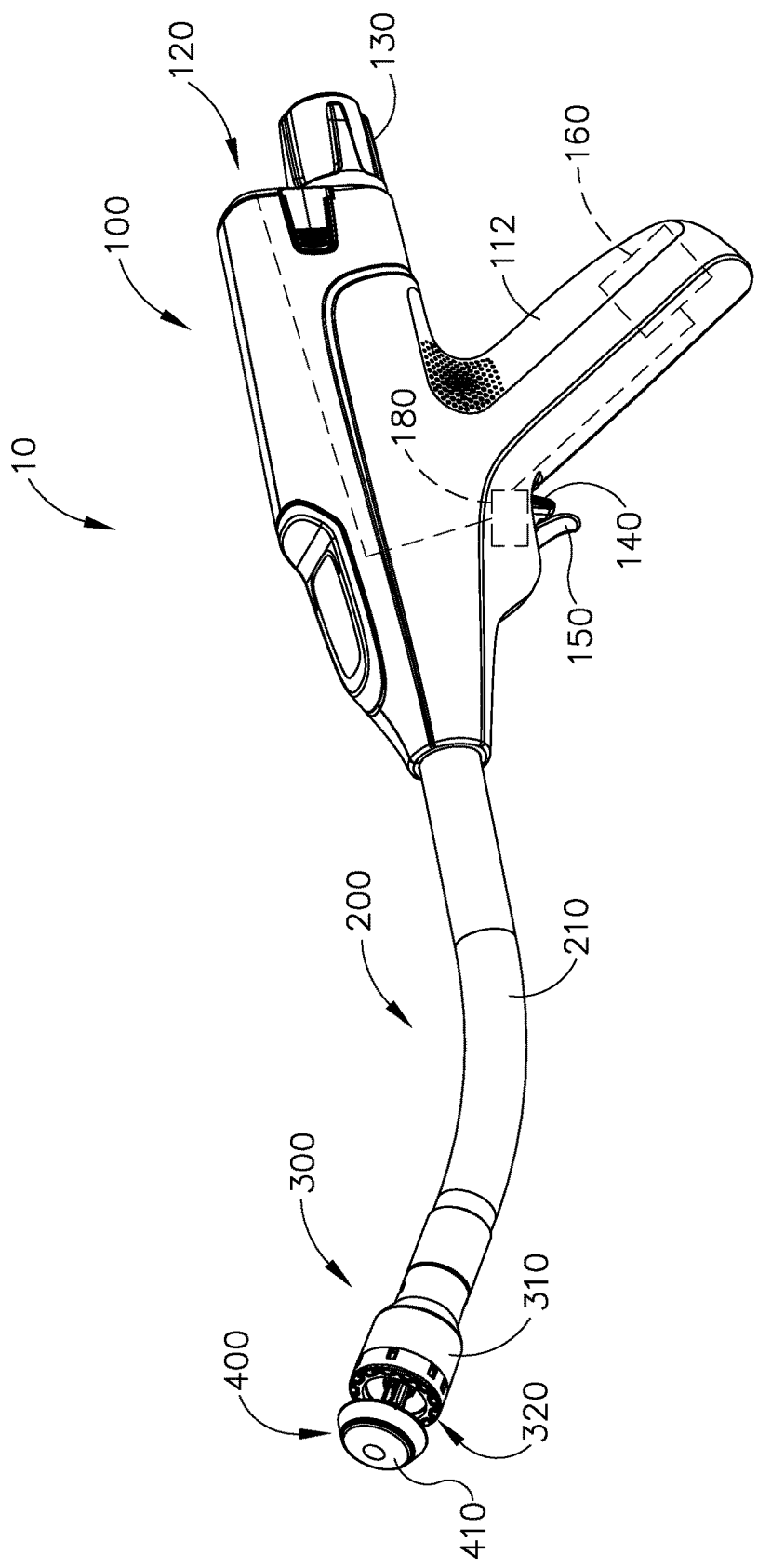
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
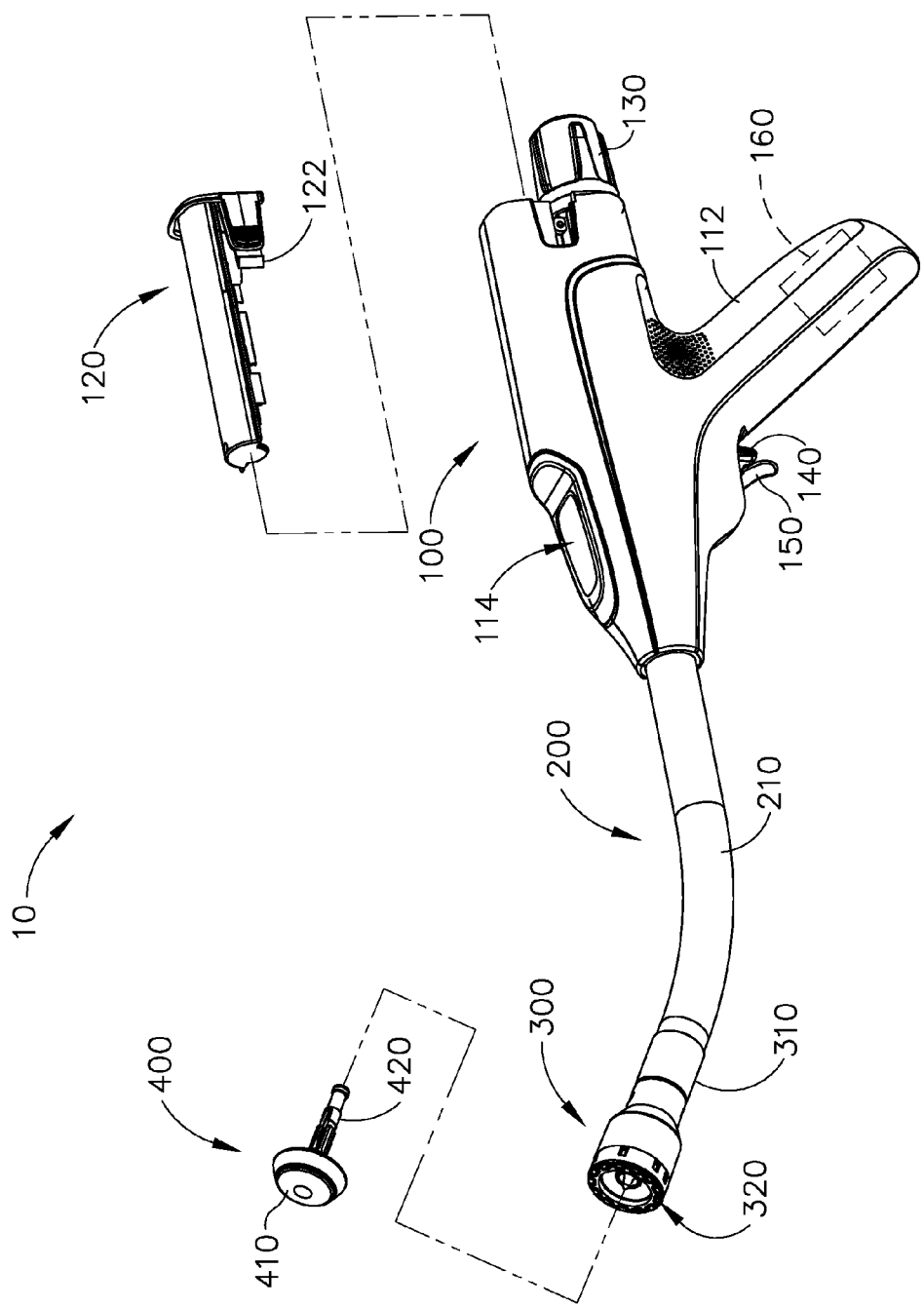
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. patent application Ser. No. 14/751,506, entitled "Anvil Stabilization Features for Surgical Stapler," filed Jun. 26, 2015, issued as U.S. Pat. No. 10,271,842 on Apr. 30, 2019; U.S. Pat. Nos. 5,205,459; 5,271,544; 5,275,322; 5,285,945; 5,292,053; 5,333,773; 5,350,104; 5,533,661; and/or 8,910, 847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
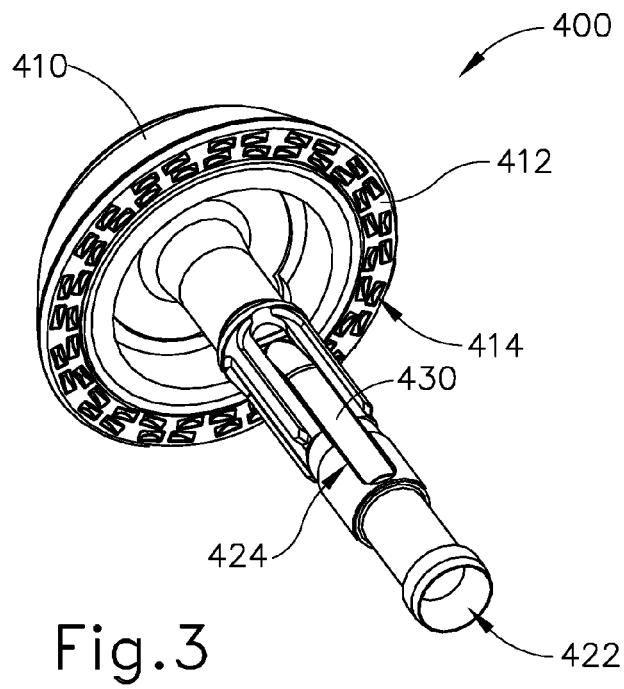
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
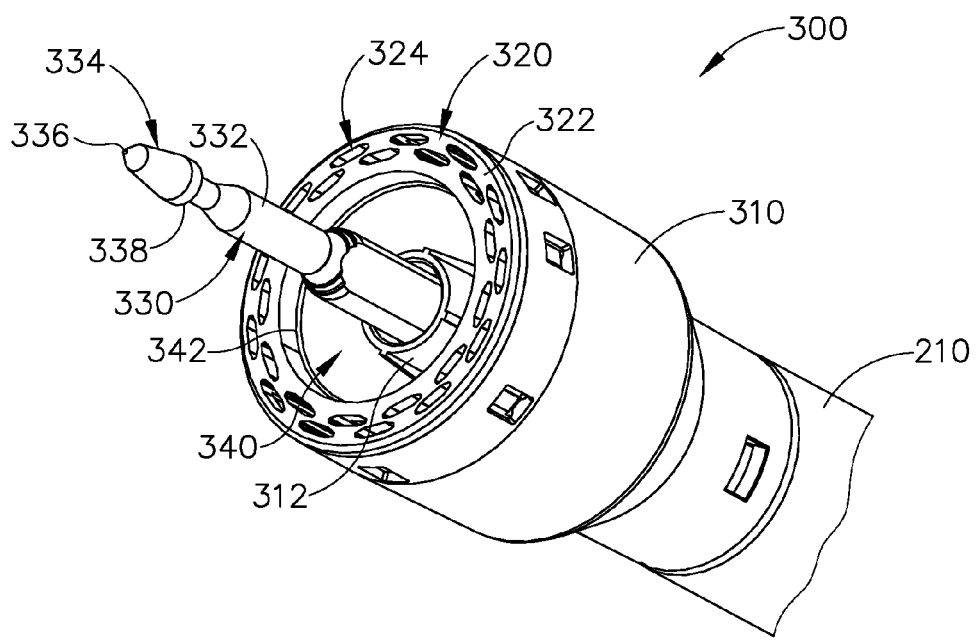
FIG. 4 depicts a perspective view of the stapling head assembly of the circular stapler of FIG. 1.
Figure 5:
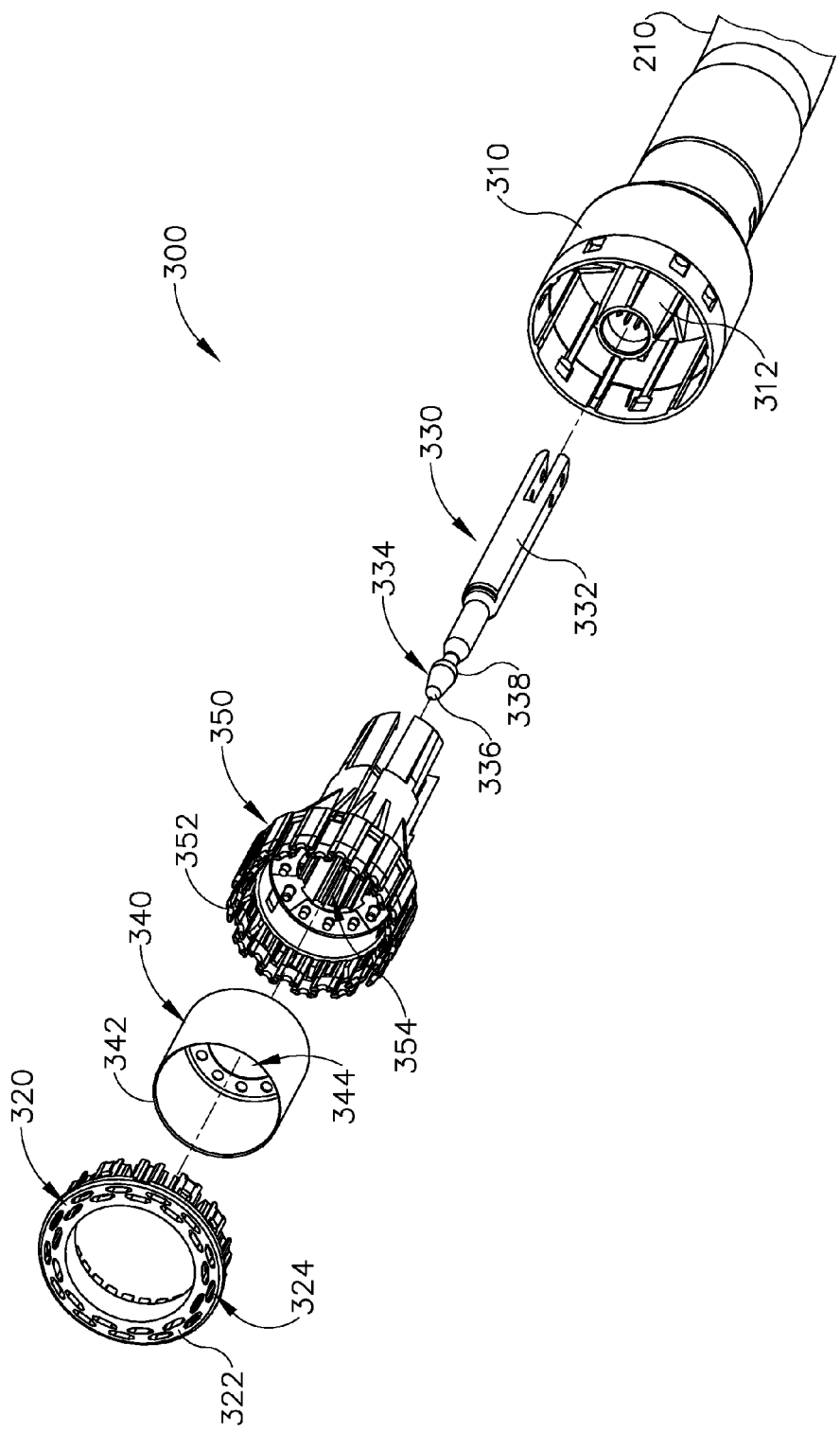
FIG. 5 depicts an exploded perspective view of the stapling head assembly of FIG. 4.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

Figure 6:
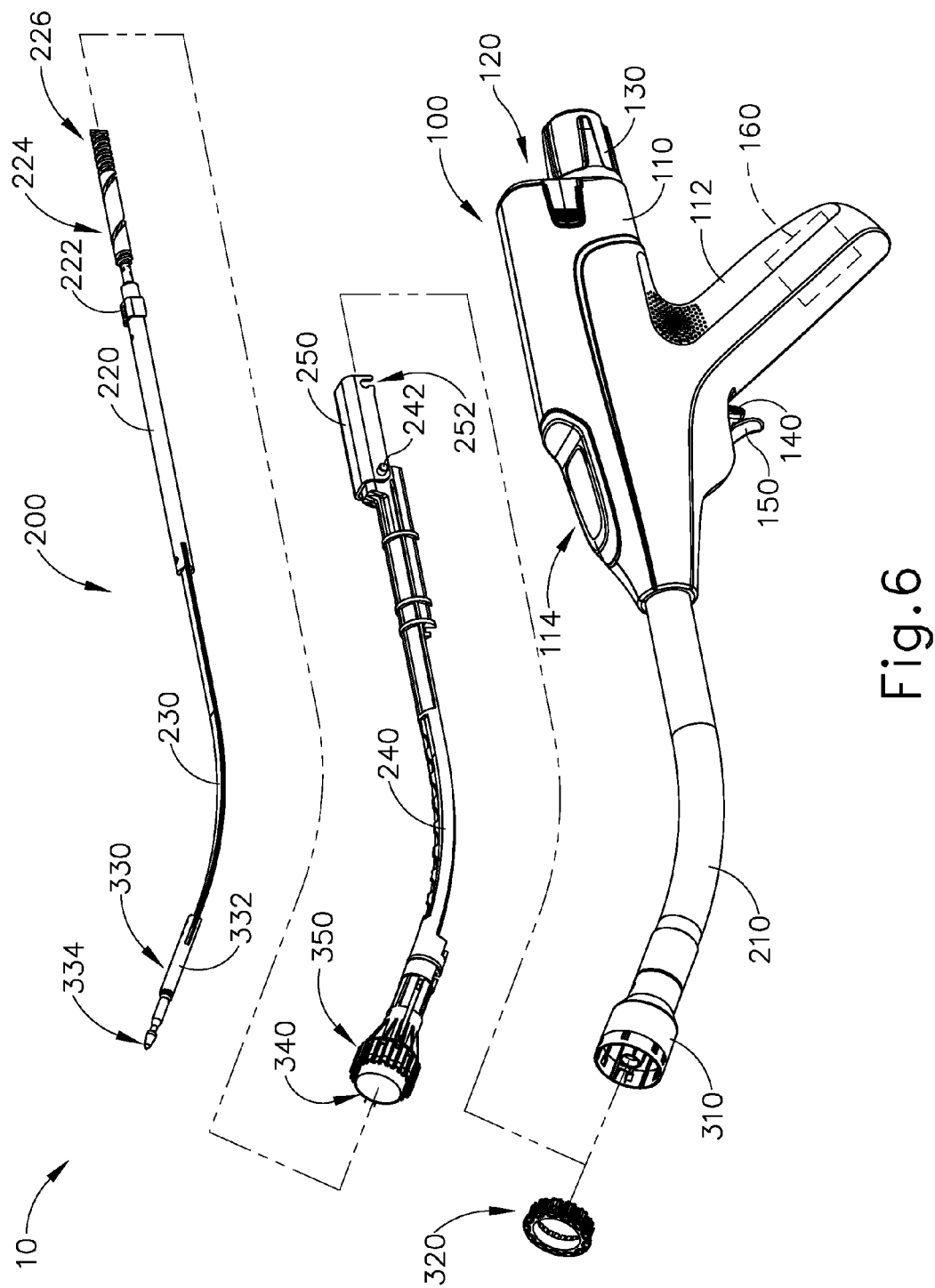
FIG. 6 depicts an exploded perspective view of the circular stapler of FIG. 1, with portions of the shaft assembly shown separately from each other.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section that is configured to facilitate positioning of stapling head assembly (300) within a patient's colon.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance between opposing surfaces (412, 322) of anvil (400) and stapling head assembly (300) until a suitable gap distance has been achieved.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle, such as the paddle shown and described in U.S. patent application Ser. No. 14/751,231, entitled "Surgical Stapler with Reversible Motor," filed Jun. 26, 2015, published as U.S. Pub. No. 2016/0374666 on Dec. 29, 2016, the disclosure of which is incorporated by reference herein. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

C. Exemplary Anastomosis Procedure with Circular Stapling Instrument

FIGS. 7-10 show an exemplary surgical procedure for providing a surgical anastomosis using instrument (10). In various instances, an anastomosis may be performed to remove a section of a patient's gastrointestinal (GI) tract. In the present example, multiple portions of a patient's colon are severed and stapled to resect a diseased portion (C') of the colon (C). The remaining severed and stapled portions of colon (C) are then anastomosed together, as discussed in further detail below.

Figure 7:
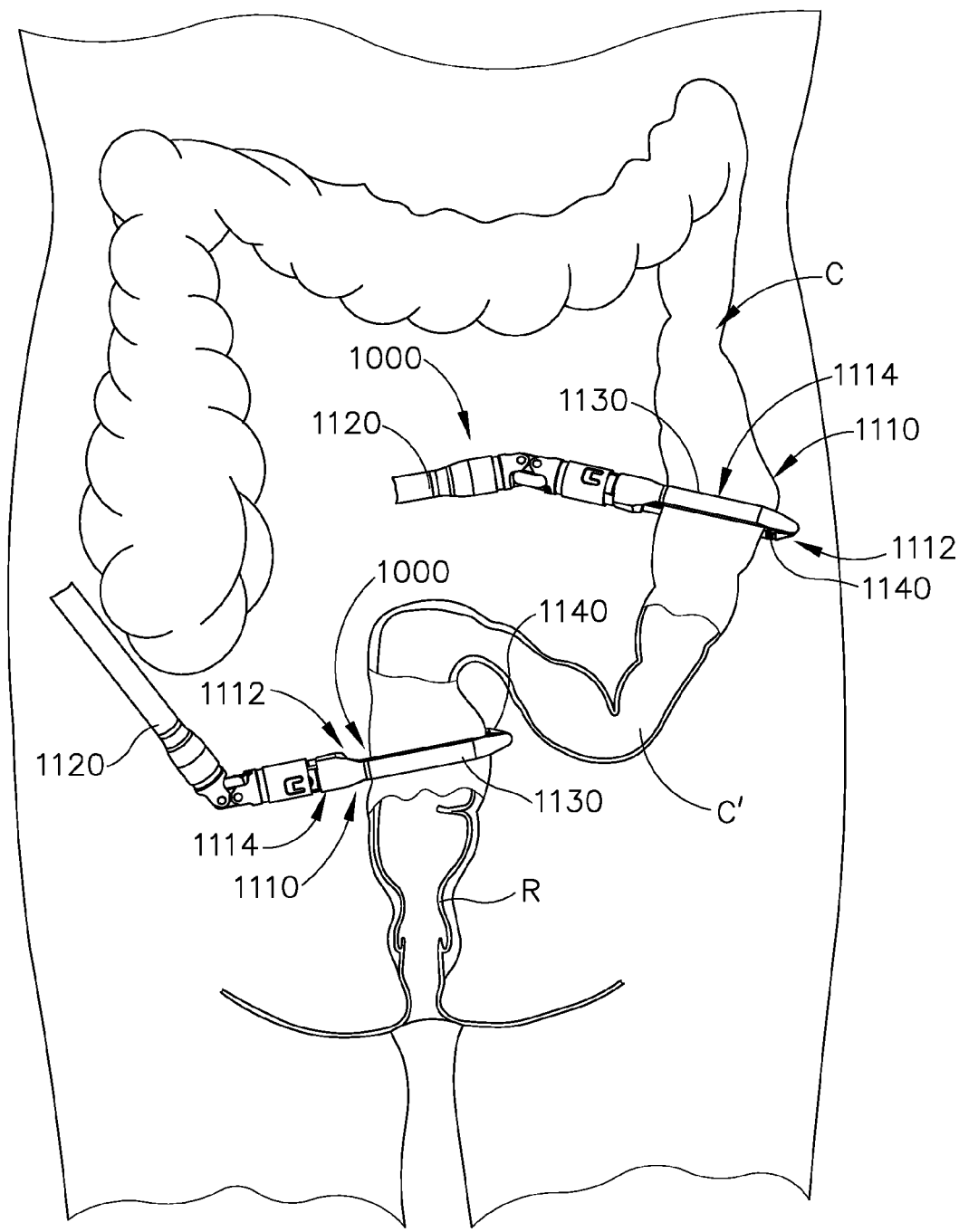
FIG. 7 depicts a schematic view of a lower portion of a patient's gastrointestinal tract, with an endocutter stapler being utilized to staple and sever the gastrointestinal tract at a first location and the endocutter stapler being utilized to staple and sever the gastrointestinal tract at a second location, thereby dividing the gastrointestinal tract into an upper portion, a transected portion, and a lower portion during a surgical procedure.

As shown in FIG. 7, multiple endocutter staplers (1000) may be inserted into a patient to sever and staple portions of the patient's colon (C). By way of example only, endocutter staplers (1000) may be constructed and operable in accordance with at least some of the teachings of U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

In the example shown, endocutter staplers (1000) are inserted into the body laparoscopically via respective trocars. Endocutter stapler (1000) comprises a shaft (1120) and an end effector (1110) extending from the shaft (1120). End effector (1110) comprises a first jaw (1112) and a second jaw (1114). First jaw (1112) comprises a staple cartridge (1140). Staple cartridge (1140) is insertable into and removable from first jaw (1112), though some variations may provide a staple cartridge that is not removable from (or at least readily replaceable from) first jaw (1112). Second jaw (1114) comprises an anvil (1130) that is configured to deform staples ejected from staple cartridge (1140). Second jaw (1114) is pivotable relative to first jaw (1112), though some variations pay provide first jaw (1112) as being pivotable relative to the second jaw (1114). Endocutter staplers (1000) may be configured ad operable in accordance with at least some of the teachings of U.S. Pub. No. 2013/0168435, entitled "Surgical Stapling Instrument with an Articulatable End Effector," published Jul. 4, 2013, the disclosure of which is incorporated by reference. While end effector (1110) is straight and is thus configured to apply a straight line of staples (185) in the present example, in other examples end effector (1110) may be curved and may thus apply a curved line of staples (185).

Figure 8:
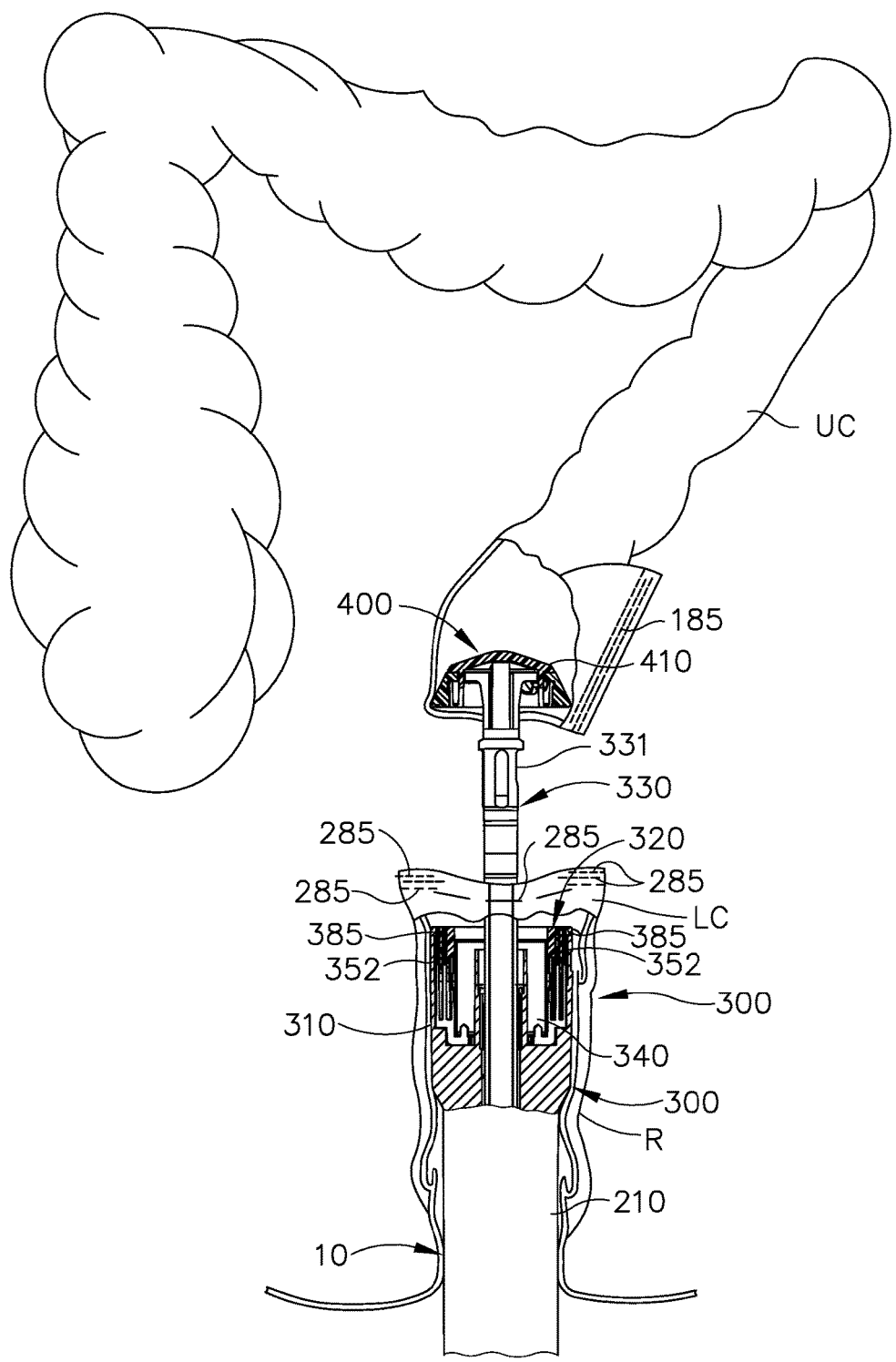
FIG. 8 depicts a schematic view of the gastrointestinal tract of FIG. 7 during another step of the surgical procedure of FIG. 7, showing the anvil of FIG. 3 positioned in the upper portion of the gastrointestinal tract and the stapling head assembly of FIG. 4 positioned in the lower portion of the gastrointestinal tract, with the anvil and the stapling head assembly and adjacent regions of the gastrointestinal tract shown in cross-section.
Figure 9:
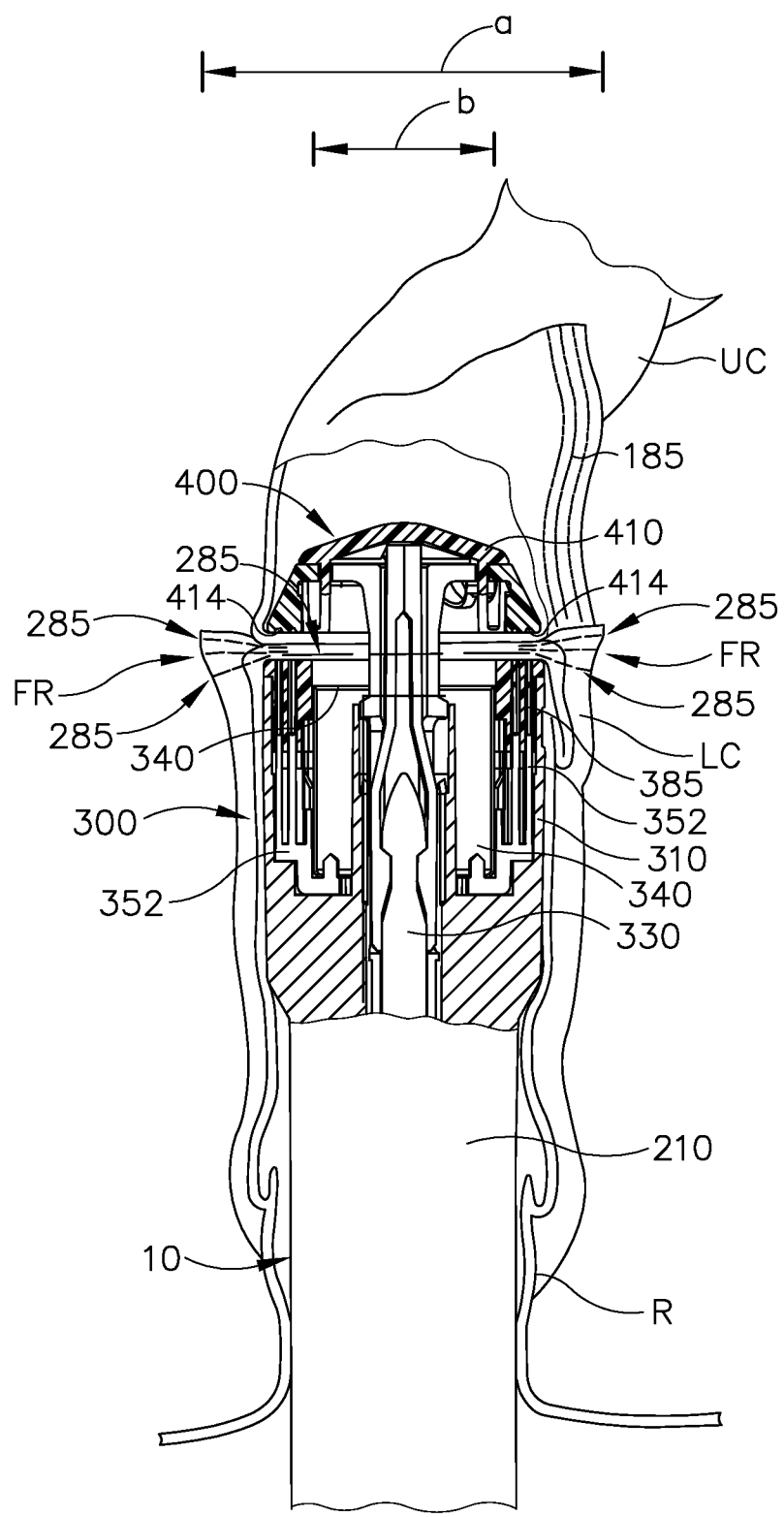
FIG. 9 depicts a schematic view of the gastrointestinal tract of FIG. 7 during another step of the surgical procedure of FIG. 7, showing the upper portion and the lower portion of the patient's gastrointestinal tract being compressed between the anvil and the stapling head assembly of the circular stapler of FIG. 1, with the anvil and the stapling head assembly and adjacent regions of the gastrointestinal tract shown in cross-section.
Figure 10:
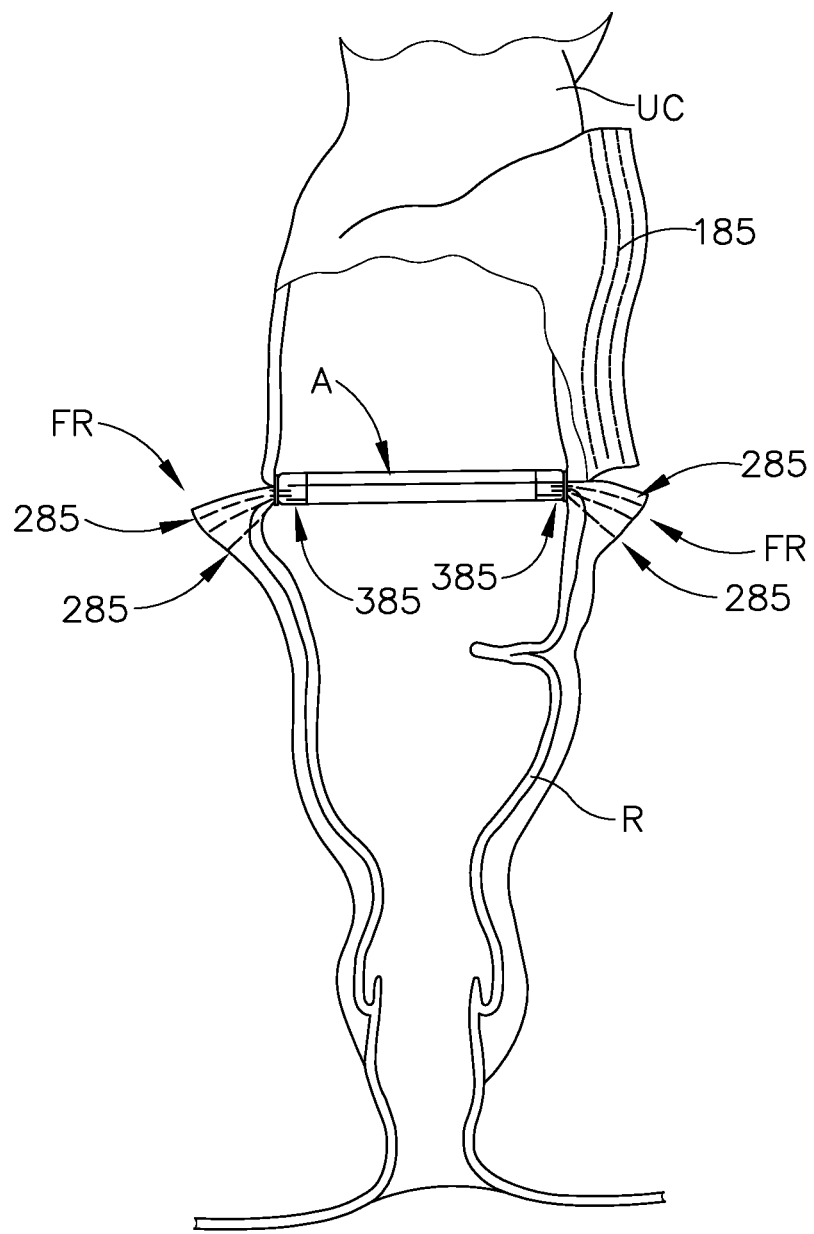
FIG. 10 depicts a schematic view of the gastrointestinal tract of FIG. 7 upon completion of the surgical procedure of FIG. 7, with the upper and lower portions of the patient's gastrointestinal tract joined by staples deployed from the circular stapler of FIG. 1, providing an anastomosis between the upper and lower portions of the patient's gastrointestinal tract, with the anastomosis and adjacent regions of the gastrointestinal tract shown in cross-section.

Anvil (1130) of endocutter stapler (1000) can be opened such that anvil (1130) and staple cartridge (1140) of endocutter stapler (1000) are positioned relative to the patient's colon (C). When anvil (1130) is moved into a closed position, anvil (1130) clamps the colon (C) against staple cartridge (1140). Turning now to FIG. 7, endocutter stapler (1000) can be operated to sever and staple the colon (C) at a first, or upper, location. In the example shown, three linear rows of staples (185) are implanted on the upper side of the severed upper portion (UC) of colon (C) and three rows of the staples (185) are implanted in the adjacent region of the diseased portion (C') of the colon (C). The same endocutter stapler (1000) (if reloaded with another cartridge (1140)), or another endocutter stapler (1000), can be operated to sever and staple the colon (C) at a second, or lower, location. In the present example, three linear rows of staples (285) implanted on the lower side of the severed lower portion (LC) of the colon (C) and three rows of staples (285) are implanted in the adjacent region of the diseased portion (C') of the colon (C). However, in other examples, other suitable configurations of staples may be implanted onto the upper portion (UC) and/or the lower portion (LC) of the colon (C). Once the colon (C) has been transected and stapled at the upper location and the lower location, the diseased portion (C') of the colon can be removed from the patient, as illustrated in FIGS. 8-10.

Referring again to FIGS. 8-9, circular stapler (10) may be utilized to anastomose the upper portion (UC) and the lower portion (LC) of the colon (C). An operator inserts a portion of shaft (210) and stapling head assembly (300) into the rectum (R) of the patient into the lower portion (LC) of the colon (C). In the example shown, a user then inserts trocar (330) through the rows of staples (285). Trocar (330) of circular stapler (10) may then be positioned in the upper portion of the colon C. In various instances, the sidewall of the upper portion of the colon C can be incised and trocar (330) can then be positioned inside the upper portion. Anvil (400) may then be directed into the upper portion of the colon (C) and connected to trocar (330) in the manner discussed above and as shown in FIG. 8.

The operator may then draw anvil (400) toward stapling head assembly (300), in the manner described above (e.g., utilizing knob (130), thus also drawing the upper colon portion (UC) toward the lower colon portion (LC). The operator may then retract trocar (330) until the tissue of the upper colon portion (UC) and the lower colon portion (LC) are compressed against deck (320) as shown in FIG. 9. It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance between opposing surfaces of anvil (400) and stapling head assembly (300) until a suitable gap distance has been achieved, such as in the manner discussed in U.S. patent application Ser. No. 14/751,506, issued as U.S. Pat. No. 10,271,842 on Apr. 30, 2019, the disclosure of which is incorporated by reference herein. As shown in FIG. 9, flap regions (FR) are formed in the lower portion (LC) of the colon (C) as anvil (400) is drawn toward stapling head assembly (300). These flap regions (FR) extend outwardly from the region of tissue compressed between anvil (400) and stapling head assembly (300).

As discussed above, stapling head assembly (300) is configured to apply annular arrays of staples (385) in the tissue captured between anvil (400) and stapling head assembly (300). Knife member (340) is advanced toward anvil (440) to sever the tissue positioned radially inwardly with respect to the annular arrays of staples (385) applied by circular stapling instrument (10). After the staples (385) have been fired and tissue has been severed, anvil (400) and stapling head assembly (300) may together be withdrawn from the patient's rectum (R). The incision that was used to insert anvil (400) into the upper portion (UC) of the colon (C) may be closed via suturing or using any other suitable technique.

As shown in FIG. 10, the upper portion (UC) of the colon (C) and the lower portion (LC) of the colon (C) are held together by the annular array of staples (385) deployed by circular stapling instrument (10). The deployed annular array of staples (385) forms an anastomosis (A) that allows fluid tight communication from the upper portion (UC) of the colon (C) to the lower portion (LC) of the colon (C). Some of staples (285) that were deployed by endocutter stapler (1000) will be removed with the tissue that was transected by knife member (340) during actuation of stapling head assembly (300). However, in this example, there are some staples (285) remaining in the outwardly projecting flap regions (FR) in the lower portion (LC) of the colon (C), outside of the anastomosis (A). This is due to the fact that the flap regions (FR) define a width (a) that is substantially greater than the diameter (b) of knife member (340), as best seen in FIG. 9. The flap regions (FR) may nevertheless remain sealed by those remaining staples (285).

II. Exemplary Apparatus and Methods for Radially Bunching a Bodily Lumen

In some instances, staples (385) that were deployed by circular stapling instrument (10) may overlap with at least some of staples (285) that were deployed by endocutter stapler (1000) in the procedure described above with reference to FIGS. 7-10. Such overlap may prevent proper formation of staples (385), which may compromise the integrity of anastomosis (A) in the long term. In addition or in the alternative, at least some of staples (285) that were deployed by endocutter stapler (1000) may interfere with compression of tissue between anvil (400) and deck member (320) and/or the traversal of knife member (340) through the tissue, which may also compromise the integrity of anastomosis (A) in the long term. Furthermore, there may be instances where the seal provided by staples (285) in flap regions (FR) of the lower portion (LC) of the colon (C) may eventually fail over time. It may therefore be desirable to provide features that prevent the outward extension of flap regions (FR) and position all of staples (285) and flap regions (FR) within the diameter (b) of knife member (340). Various examples of such features will be described in greater detail below.

A. Exemplary Alternative Staple Cartridge Including Resilient Buttress

Figure 11:
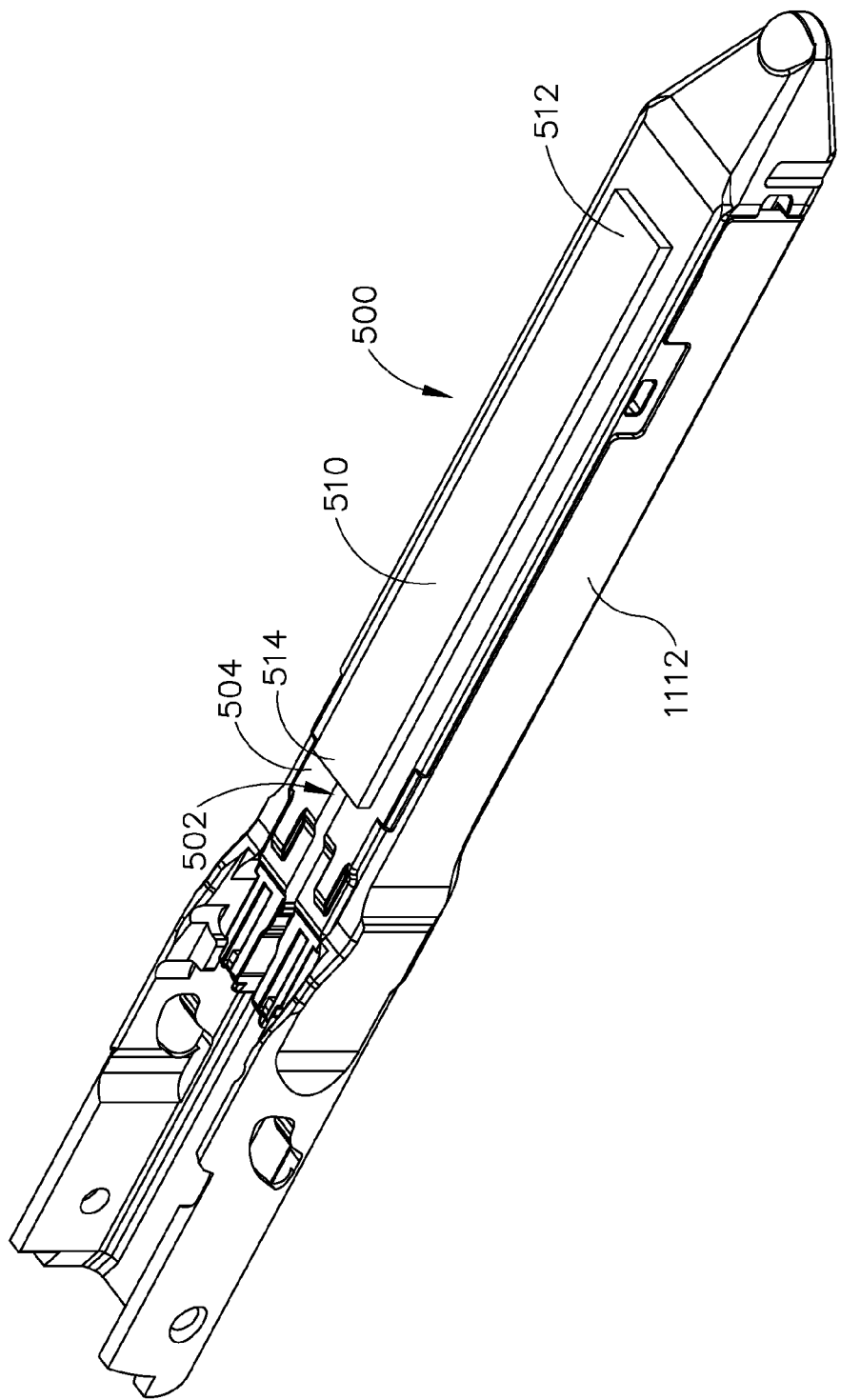
FIG. 11 depicts a perspective view of an exemplary alternative staple cartridge loaded into the lower jaw of the stapling device of FIG. 7, including a buttress on a deck thereof, capable of being utilized in the procedure shown in FIGS. 7-10.

FIG. 11 shows an exemplary alternative staple cartridge (500) inserted in first jaw (1112) of end effector (1110). Staple cartridge (500) is substantially similar to staple cartridge (1140), except that staple cartridge (500) includes two rows of staple cavities (not shown) on each side of slot (502) of instead of three rows. Therefore, when staple cartridge (500) is incorporated into end effector (1110), two rows of staples (520) are implanted onto opposing, severed portions of tissue rather than three rows of staples (520). Moreover, staple cartridge (500) includes a buttress (510) that is removably secured to deck (504) of staple cartridge (500). By way of example only, buttress (510) may be secured to deck (504) in accordance with any of the teachings of U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. Other suitable ways in which buttress (510) may be secured to deck (504) will be apparent to those of ordinary skill in the art in view of the teachings herein.

Buttress (510) of the present example has a first end (512) and a second end (514). Buttress (510) is formed of an elastic material that is resiliently biased to assume a longitudinally contracted configuration. In FIG. 11, buttress (510) is elongated from its natural position while fixed to deck (504). It should therefore be understood that buttress (510) is resiliently biased to longitudinally contract from the configuration shown in FIG. 11, to draw ends (401, 402) toward each other. It should also be understood that the means used for connecting buttress (510) to deck (504) imparts a force on buttress (510) to prevent buttress (510) from contracting to its natural length. As shown in FIG. 11, buttress (510) is planar and is adhered to deck (504) using an adhesive material in the configuration of FIG. 11, where buttress (510) has a maximum width that is less than a minimum width of deck (504) in the configuration of FIG. 11.

Figure 12B:
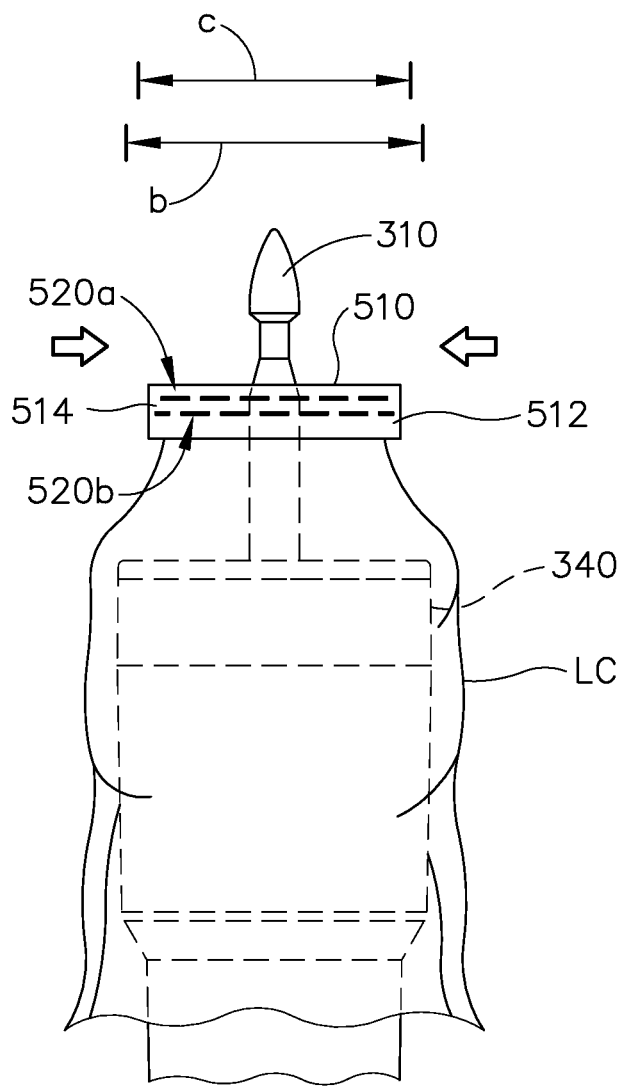
FIG. 12B depicts a side elevational view of portion of the gastrointestinal tract after having been stapled and severed utilizing the staple cartridge of FIG. 11, with the buttress in a contracted configuration.

As mentioned above, staple cartridge (500) may be implemented in endocutter stapler (1000). Therefore, endocutter stapler (1000) may drive a plurality of staples through deck (504) and buttress (510) onto the severed lower portion (LC) of the colon (C) as shown in FIGS. 12A-12B. When staples (520) are driven from cartridge (500), buttress (510) will be captured between the crowns of the driven staples (520) and the adjacent tissue. While the means used for connecting buttress (510) to deck (504) imparts a force on buttress (510) that is sufficient to prevent buttress (510) from contracting to its natural length, the means used for connecting buttress (510) to deck (504) nevertheless also allows driven staples (520) to pull buttress (510) away from deck (504) without significantly damaging buttress (510). FIGS. 12A-12B show buttress (510) detached from deck (504) and secured to tissue by a first row of staples (520a) and a second row of staples (520b). In the current example, first row of staples (520a) and second row of staples (520b) are formed, however any suitable number of staple rows may be used, such as three or four rows of staples. It should also be understood that endocutter stapler (1000) has simultaneously transected and sealed the lower portion (LC) of colon (C) with a blade and staples (520), respectively, in accordance with conventional endocutter stapler operation.

Once buttress (510) detaches from deck (504), there is no longer a force imparted on buttress (510) preventing buttress (510) from contracting to its natural length. FIG. 12A shows buttress (510) secured to the lower portion (LC) of the colon (C) by staples (520), immediately after buttress (510) is detached from deck (504), before buttress (510) has had time to contract to its natural position. In this state, the flap regions (FR) define a width (a) that is substantially greater than the diameter (b) of knife member (340), as described above.

Figure 12C:
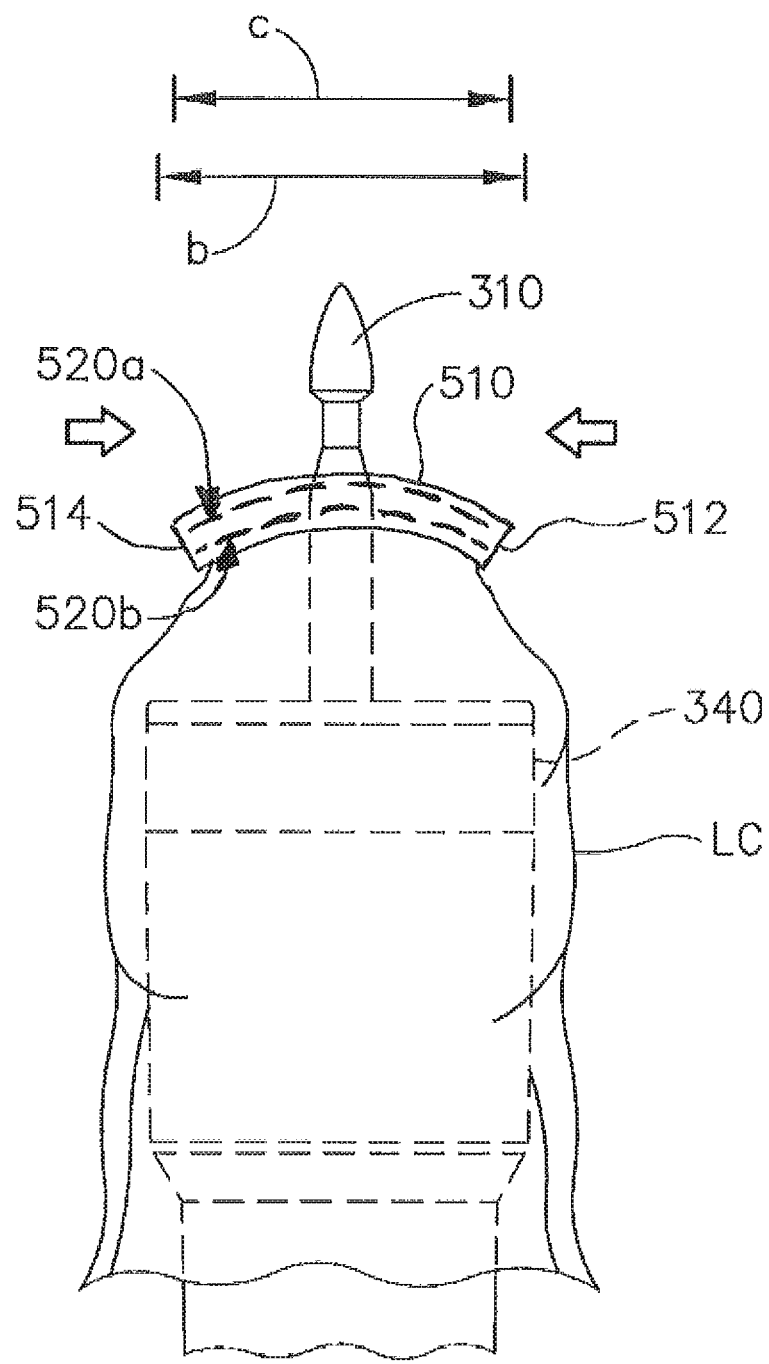
FIG. 12C depicts a side elevational view of a portion of the gastrointestinal tract after having been stapled and severed utilizing the staple cartridge of FIG. 11, with the buttress in a contracted configuration forming an arch.

FIGS. 12B-12C show buttress (510) in the contracted configuration. As mentioned above, since buttress (510) is detached from deck (504), there is no longer a force elongating buttress (510), such that first end (512) and second end (514) are allowed to contract toward each other. First end (512) and second end (514) of buttress (510) may contract toward each other in a linear fashion as shown in FIG. 12B (e.g., such that the contracted form of buttress (510) is still linear), a coiling fashion (e.g., such that the contracted form of buttress (510) forms a coil), in an arching fashion as shown in FIG. 12C (e.g., such that the contracted form of buttress (510) forms an arch), in a wave-like fashion (e.g., such that the contracted form of buttress (510) forms a wave-like configuration), or in any other suitable manner as will be apparent to a person having ordinary skill in the art in view of the teachings herein. Depending on material used, it is envisioned that buttress (510) may contract at any multitude of suitable rates.

Since first staple line (520a) and second staple line (520b) are attached to buttress (510), the distance from each staple in first and second staple line (520a, 520b) decreases as well. In particular, the contraction of buttress (510) has transversely contracted the severed end of the lower portion (LC) of the colon (C), such that the severed end of the lower portion (LC) of the colon (C) defines a contracted width (c). This contracted width (c) is smaller than the diameter (b) of knife member (340). It should be understood that there are gaps defined between adjacent staples (520) while staples (520) are still in cartridge (500), and that these gaps will allow staples (520) to move with the contracting buttress (510).

Figure 13A:
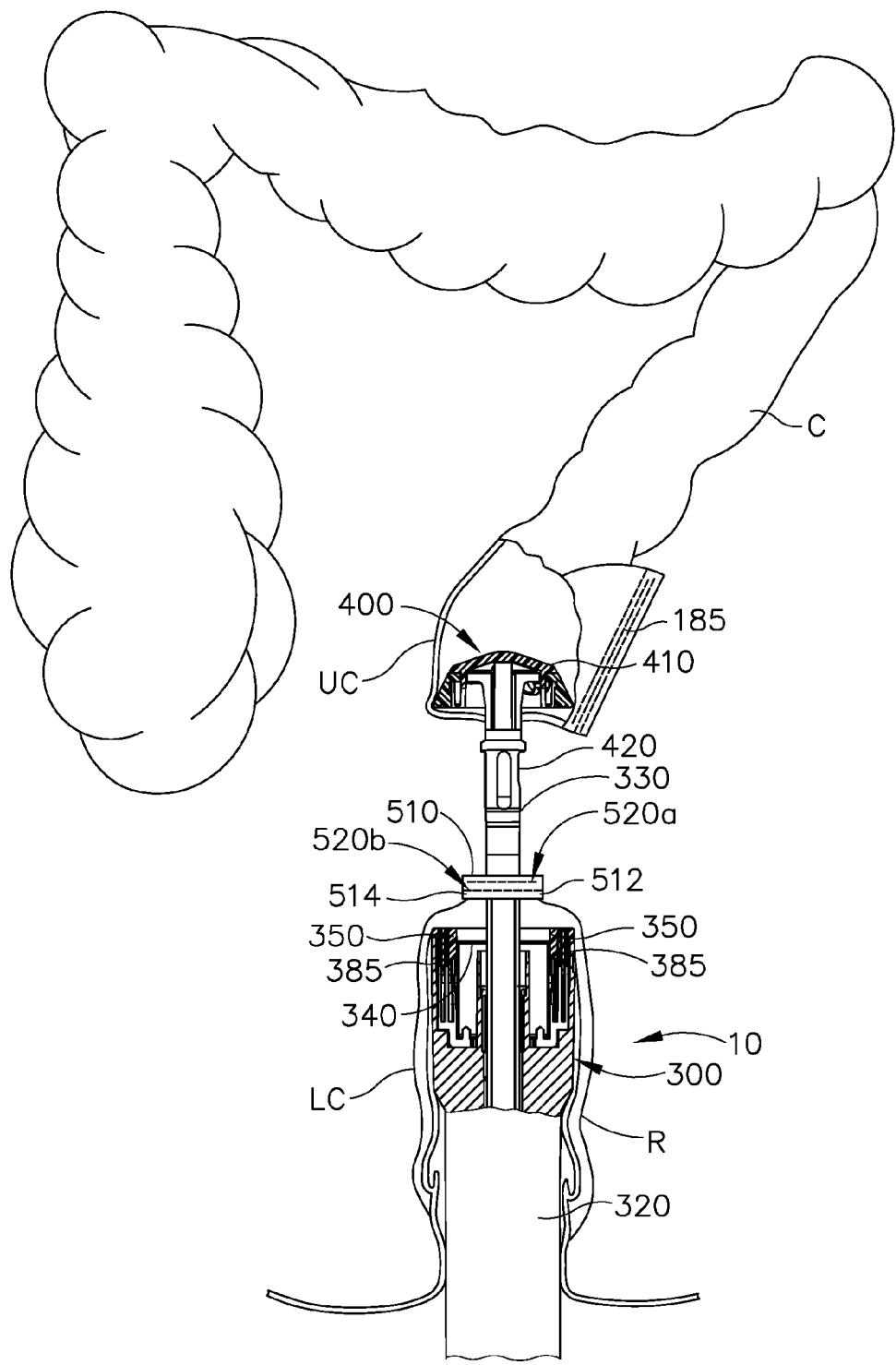
FIG. 13A depicts a schematic view of severed upper and lower portions of a patient's gastrointestinal tract, with an anvil of the circular stapler of FIG. 1 positioned in the upper portion of the gastrointestinal tract and a shaft of the circular stapler of FIG. 1 positioned in the lower portion of the gastrointestinal tract, with the staple cartridge of FIG. 11 having been used to staple and sever the gastrointestinal tract, and with severed end of the lower portion of the gastrointestinal tract in a contracted configuration, during a surgical procedure.
Figure 13B:
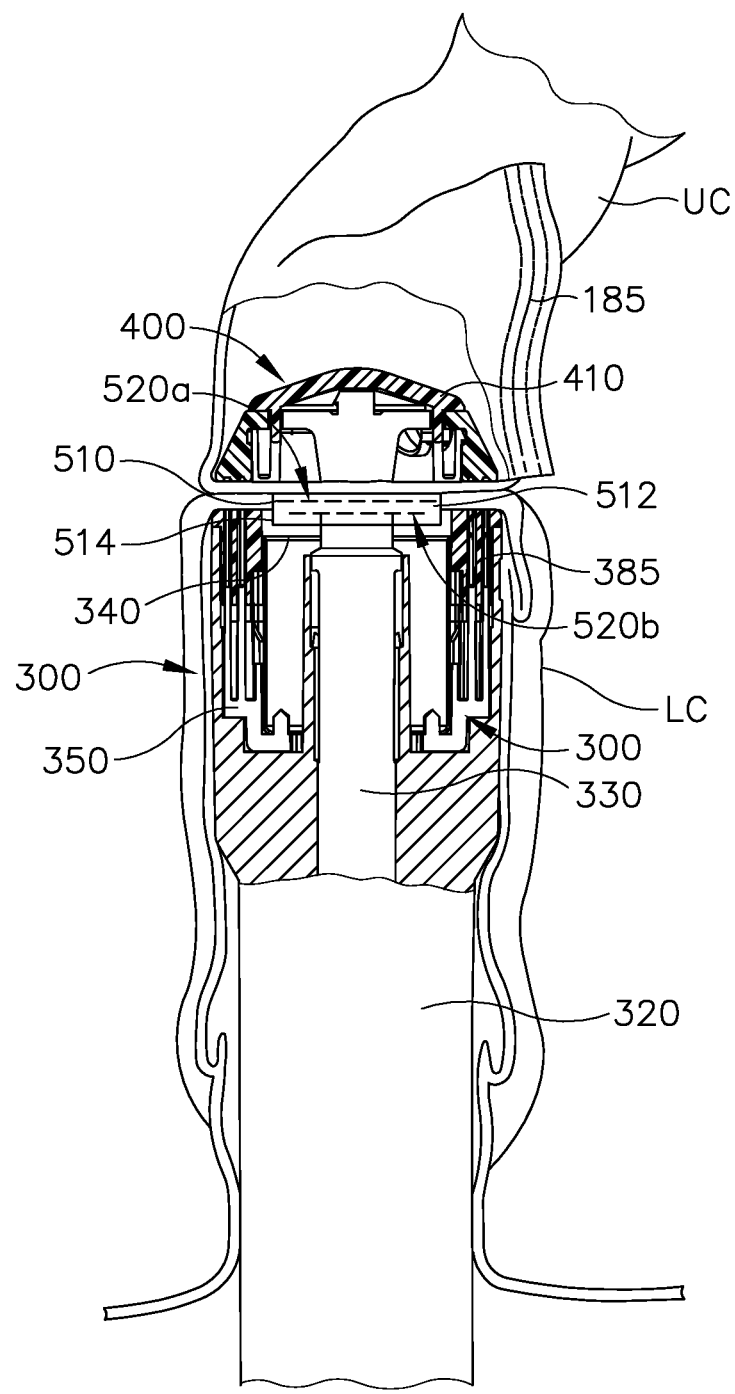
FIG. 13B depicts a schematic view of the gastrointestinal tract of FIG. 13A during another step of the surgical procedure of FIG. 13A, showing the upper portion and the lower portion of the patient's gastrointestinal tract being compressed between the anvil and the stapling head assembly of the circular stapler of FIG. 1, with the anvil and the stapling head assembly and adjacent regions of the gastrointestinal tract shown in cross-section.
Figure 13C:
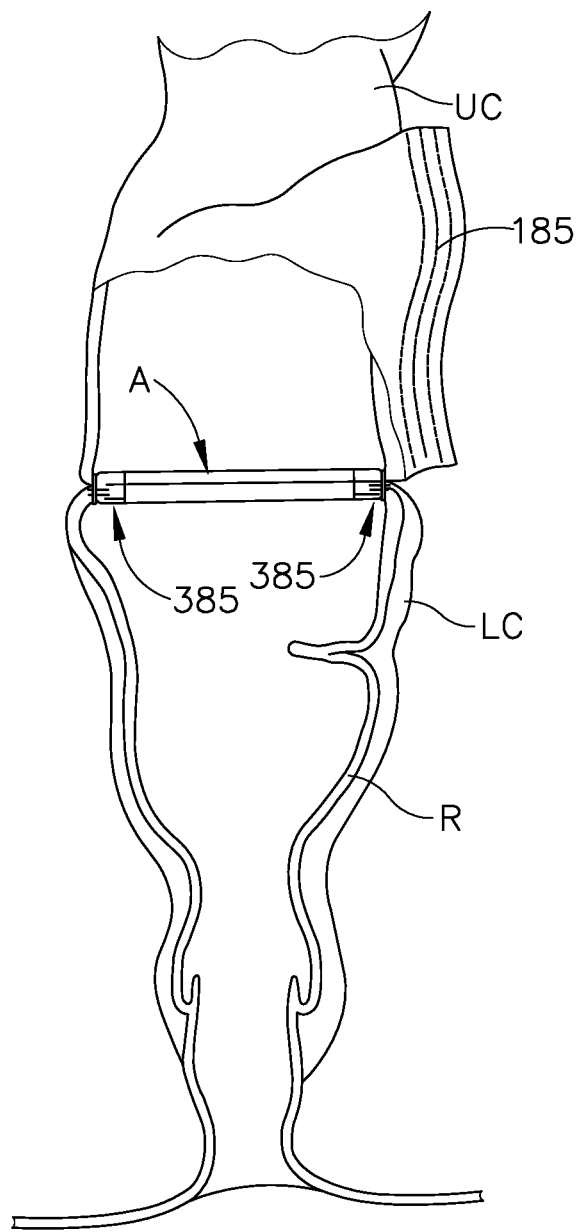
FIG. 13C depicts a schematic view of the gastrointestinal tract of FIG. 13A upon completion of the surgical procedure of FIG. 13A, with the upper and lower portions of the patient's gastrointestinal tract joined by staples deployed from the circular stapler of FIG. 1, providing an anastomosis between the upper and lower portions of the patient's gastrointestinal tract, with the anastomosis and adjacent regions of the gastrointestinal tract shown in cross-section.

FIGS. 13A-13C show steps of an anastomosis procedure similar to the procedure shown in FIGS. 7-10. Upper colon portion (UC) and lower colon portion (LC) are shown to have been severed and stapled in a similar manner to that shown in FIGS. 7-8. However, at least the lower colon portion (LC) has been severed and stapled utilizing staple cartridge (500). Lower colon portion (LC) therefore includes staples (520) and buttress (510) coupled thereto in the manner discussed above. As shown, a portion of shaft (210) and stapling head assembly (300) are inserted into the rectum (R) of the patient and into the lower portion (LC) of the colon (C). In the example shown, trocar (330) is passed through the lines of staples (520) such that trocar (330) is exposed out of lower colon portion (LC). Anvil (400) is shown to be positioned in the upper portion (UC) of the colon (C), with shank (420) extending through an opening of the upper colon portion (UC). At this stage, buttress (510) is in the contracted state shown in FIG. 12B, resulting in the lines of staples (520) and the severed portion of the lower colon portion (LC) being drawn inwardly toward trocar (330). Thus, the tissue has the effective width (c) that is smaller than the diameter (b) of knife member (340), such that staples (520), buttress (510), and flap regions (FR) are all positioned within the cylindrical plane defined by knife member (340).

The operator then connects shank (420) to trocar (330) in the manner discussed above. As shown in FIG. 13B, the operator may then draw anvil (400) toward stapling head assembly (300), in the manner described above (e.g., utilizing knob (130)), thus also drawing the upper colon portion (UC) toward the lower colon portion (LC). The operator may then retract trocar (330) until the tissue of the upper colon portion (UC) and the lower colon portion (LC) are compressed against the deck member (320) to achieve a desirable gap distance, as shown in FIG. 13B and discussed above.

The operator may then actuate trigger (150) to actuate stapling head assembly (300), resulting in the stapling and severing of tissue in a similar manner as shown in FIG. 9. Due to the staples (520), buttress (510), and flap regions (FR) all being positioned within the cylindrical plane defined by knife member (340), the combination of staples (585), buttress (510), and flap regions (FR) are all severed from the adjacent tissue. Thus, no staples (520) or components of buttress (510) are disposed in the tissue that remains at the resulting anastomosis (A) site as shown in FIG. 13C. Moreover, staples (520) do not impede the successful operation of circular stapler (10), and there are no flap regions (FR) extending outwardly from the anastomosis (A) site. The severed portion of tissue including staples (520) and buttress (510) may be removed by the operator via the patient's rectum.

B. Exemplary Exterior Pleating Member with Wire Guide

Figure 14:
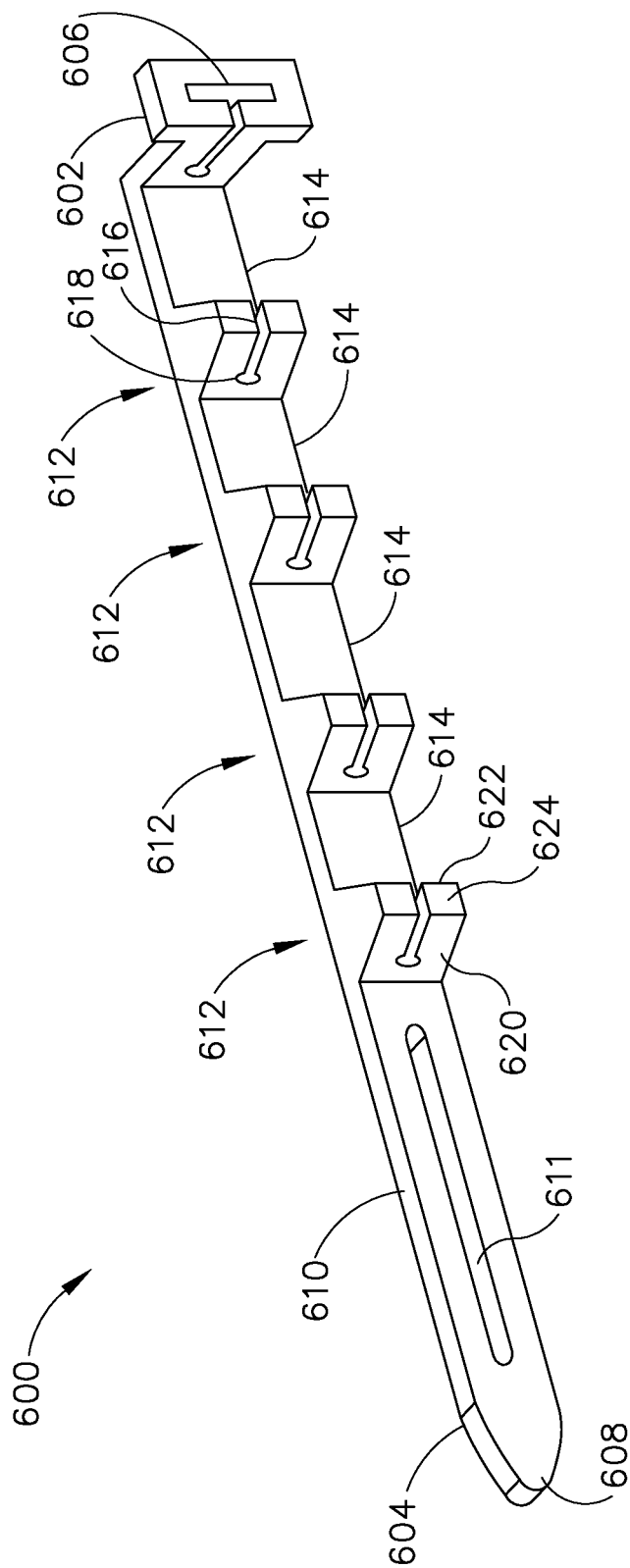
FIG. 14 depicts a perspective view of an exemplary bendable pleating member.

FIGS. 14-16B show another feature that may be used to prevent the outward extension of flap regions (FR) and position all of the tissue at the severed end of lower colon portion (LC) within the diameter (b) of knife member (340). In particular, FIGS. 14-16B show a bendable pleating member (600) that may be used to contract a bodily lumen such as the colon (C) inwardly, while forming an angularly spaced array of pleats in the bodily lumen. As best seen in FIG. 14, bendable pleating member (600) includes a pulling end (604), a first bendable body (610) unitarily connected to a second bendable body (614), and a receiving end (602). Pulling end (604) includes a tapered portion (608). Receiving end (602) includes a slot (606) that is configured to receive pulling end (604). Tapered portion (608) is narrower compared to the remaining portion of pulling end (604) in order to better allow an operator to guide pulling end (604) within the confines of slot (606). As pulling end (604) travels through slot (606) of receiving end (602), first and second bendable bodies (610, 614) bend form a circumferential path. As shown in FIGS. 15A-16B, bendable pleating member (600) is dimensioned to encompass a bodily lumen, such as colon (C), when forming the circumferential path. The farther pulling end (604) travels through slot (606) of receiving end (602), the smaller the circumferential path becomes.

First bendable body (610) includes an entry channel (611) that is configured to initially receive a wire (660), while second bendable body includes a plurality of individual protrusions (612) that are also configured to receive wire (660). The structure of wire (660) will be described in greater detail below. The current example of bendable pleating member (600) shows four individual protrusions (612). However, any suitable number of individual protrusions (612) may be utilized as will be apparent to one having ordinary skill in the art in view of the teachings herein. Each individual protrusion (612) includes an angled entry face (622), an angled exit face (620), a contact face (624) defined by angled entry face (622) and angled exit face (620), a wire guide channel (618) extending from angled entry face (622) through angled exit face (620), and a wire exit (626) extending from wire guide channel (618) to contact face (624). Receiving end (602) also includes wire guide channel (618) and wire exit (616) for initial introduction of wire (660) to individual protrusions (612).

Figure 15A:
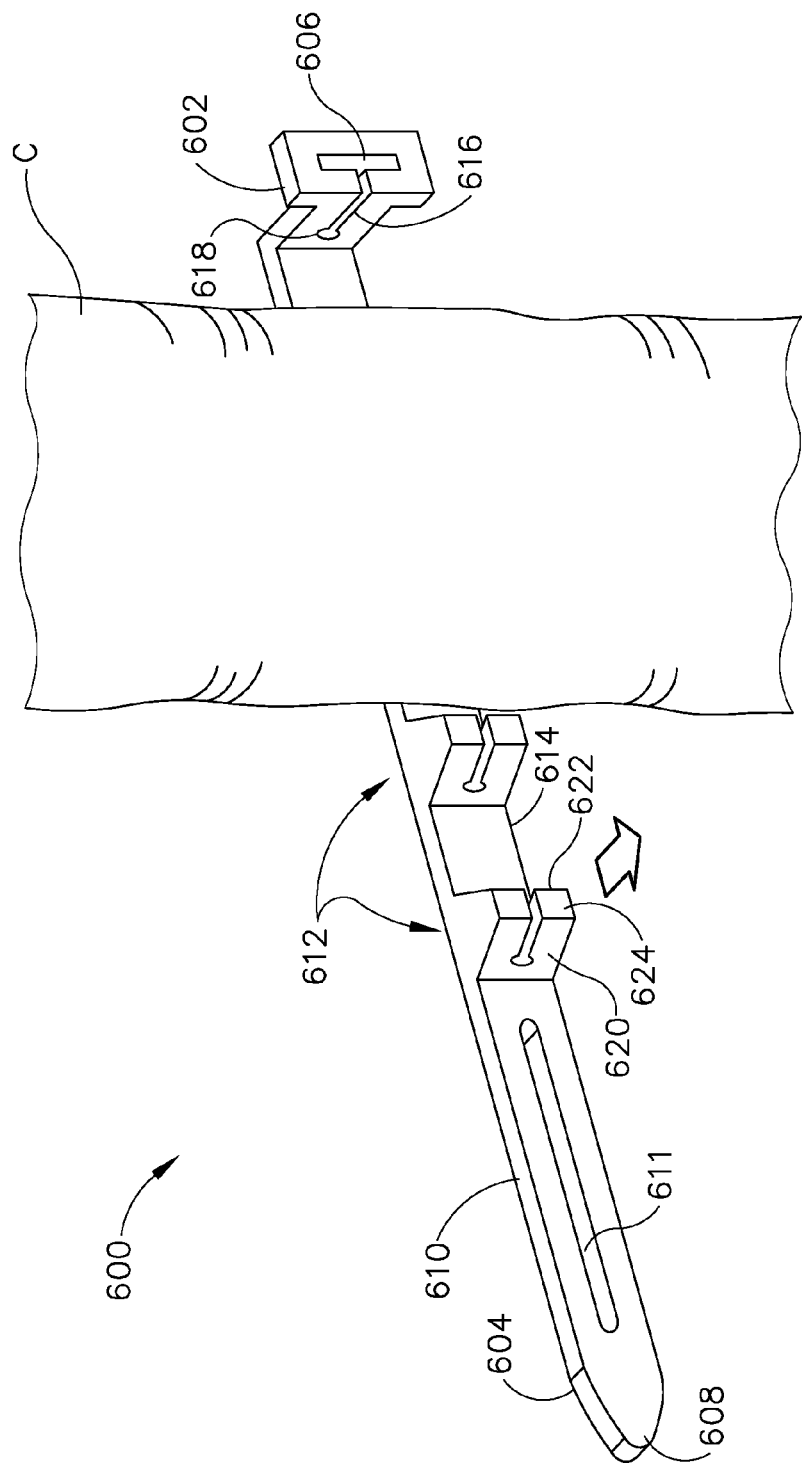
FIG. 15A depicts a perspective view of the bendable pleating member of FIG. 14 positioned adjacent to the colon of a patient.
Figure 15B:
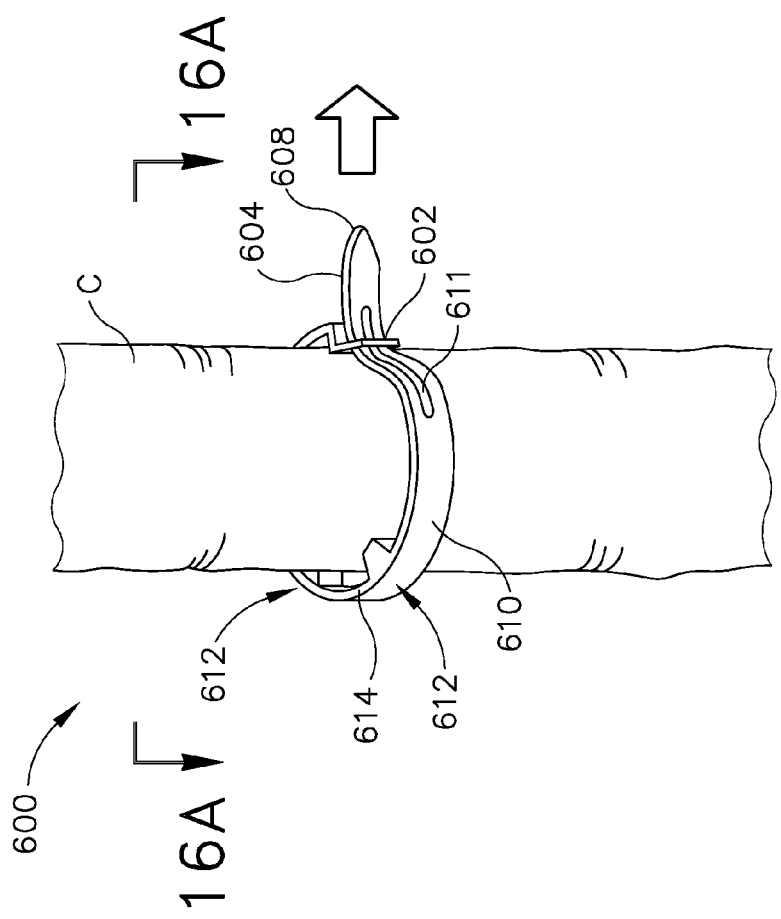
FIG. 15B depicts a perspective view of the bendable pleating member of FIG. 14 wrapped around the colon of the patient.
Figure 16A:
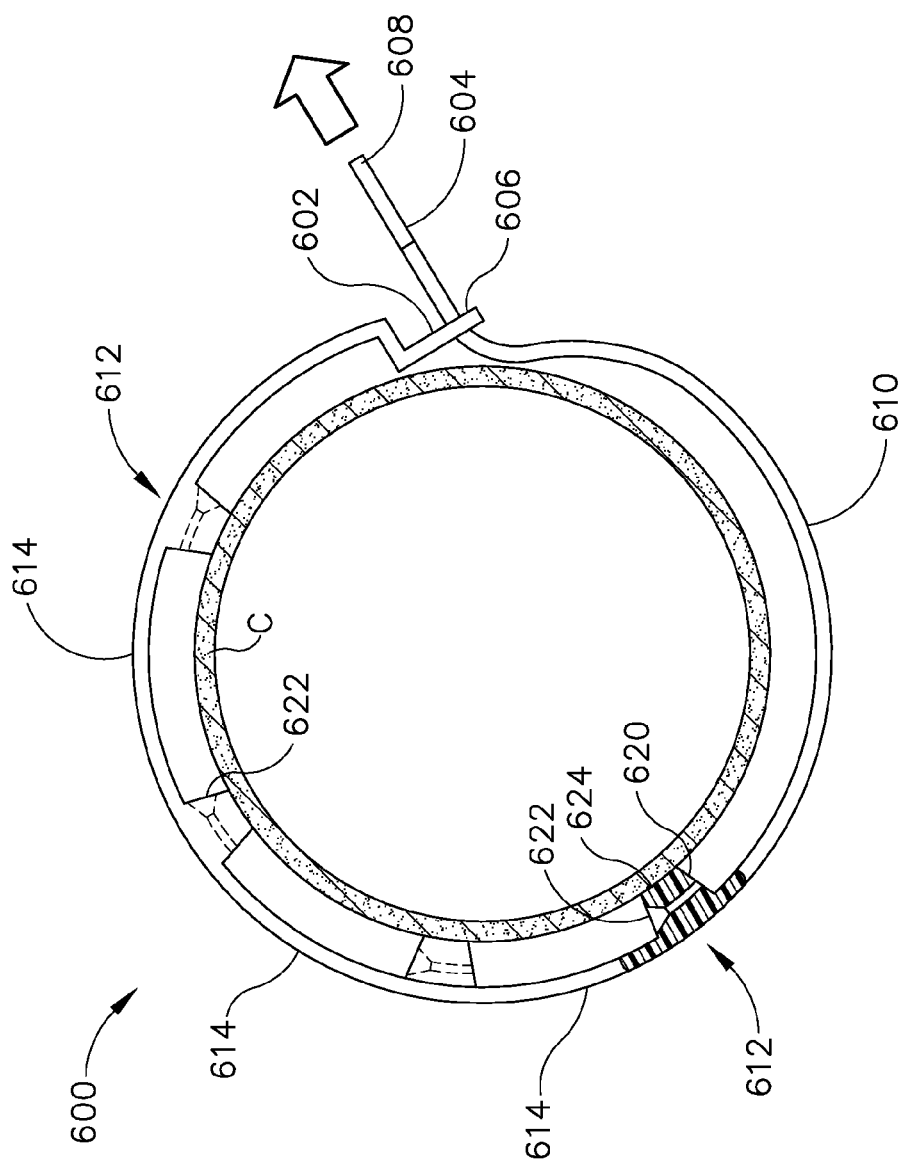
FIG. 16A depicts a cross-sectional end view of the bendable pleating member of FIG. 14 wrapped around the colon of the patient, taken along line 16A-16A of FIG. 15B.
Figure 16B:
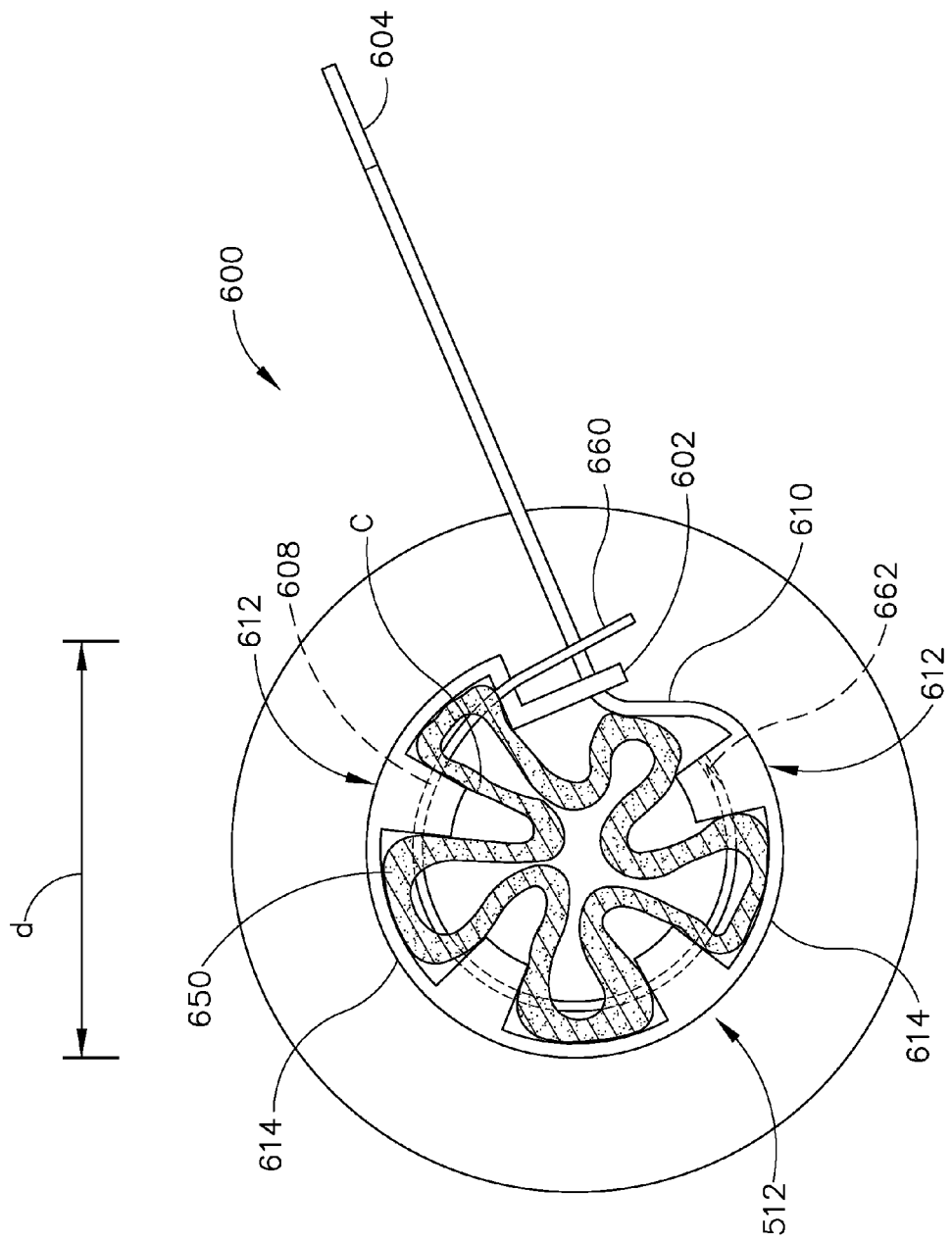
FIG. 16B depicts a top cross-sectional view of the bendable pleating member of FIG. 14 cinched around the colon of a patient, taken along line 16B-16B of FIG. 15C, with a wire inserted into a guide path defined by the cinched bendable pleating member of FIG. 14.

FIGS. 15A-16B show pleating member (600) being wrapped about colon (C). As shown, pleating member (600) is dimensioned to encompass colon (C). It should be understood that the process shown in FIGS. 15A-16B may be performed before endocutter staplers (1000) are used to transect the colon (C) as described above with reference to FIG. 7. Pleating member (600) is initially placed adjacent to the colon (C) as shown in FIG. 15A, and then pulling end (604) is passed through slot (606) of receiving end (602) to wrap pleating member (600) about the colon (C) as shown in FIGS. 15B and 16A. As pulling end (604) is further pulled through slot (606) of receiving end (602), the circumference defined by pleating member (600) decreases as shown in FIGS. 15C and 16B.

As the circumference defined by pleating member (600) decreases, pleating member (600) bears inwardly on the colon (C) and thereby reduces the diameter of the colon (C) at the region being engaged by pleating member (600). In particular, contact faces (624) of protrusions (612) provide focused pressure on adjacent regions about the circumference of the colon (C). The tissue of the colon (C) may eventually engage angled faces (620, 622) of protrusions (612). The trapezoidal configuration of protrusions (612) ultimately causes pleats (650) to form in a bunched-up region of the colon (C), as also shown in FIGS. 15C and 16B. The reduced diameter (d) of the bunched-up region of the colon (C) is smaller than the diameter (b) of knife member (340). Thus, the bunched-up tissue containing pleats (650) will fit within the cylindrical plane defined by knife member (340).

With pleating member (600) being held in the constricting configuration shown in FIGS. 15C and 16B, wire (660) is introduced into entry channel (611). Wire (660) of the present example has a sharp distal tip (662) (e.g., similar to a needle) and a flexible body. The body of wire (660) has sufficient column strength to enable wire (660) to be pushed through the tissue of the colon (C); yet wire (660) also has enough flexibility to enable wire (660) to traverse an arcuate path as described below.

Entry channel (611) is located along pulling end (604) and first bendable body (610) in such a way as to align with wire guide channel (618) of receiving end (602) when pleating member (600) is in the constricting configuration. Additionally, each wire guide channel (618) aligns to define an arcuate path for wire (660). Wire guide channel (618) is also located on each angled entry face (622) and angled exit face (620) so that wire (660) penetrates colon (C) while traveling along the arcuate path. In other words, wire (660) is capable of traveling from entry channel (611), through the arcuate path defined by each wire guide channel (618). Due to the combination of the formation of pleats (650) and the arcuate travel of wire (660), wire is disposed in the tissue of the colon (C) in a manner similar to a purse-string suture. This arrangement is shown in FIG. 16B, with wire (660) passed through the pleats (650) formed in the tissue of the colon (C).

Once wire (660) has traveled along the complete arcuate path defined by the combination of wire guide channels (618), pulling end (604) may be retracted out of slot (606), allowing bendable pleating member (600) may be removed from colon (C). In the present example, wire (660) will not be disturbed by the removal of bendable pleating member (600) because wire exits (616) provide a path for wire (660) to disconnect from bendable pleating member (600) while wire (660) remains disposed in the tissue of the colon (C). With bendable pleating member (600) removed, wire (660)

remains in place to hold the tissue of the colon (C) in the bunched-up configuration, maintaining the presence of pleats (650).

In an exemplary use, pleating member (600) is used to bunch-up, pleat, and guide wire (660) into a lower portion (LC) of the colon (C) that is between a diseased portion (C') of the colon (C) and the patient's rectum (R). The operator may then use an endocutter stapler (1000) to separate an upper region of the diseased portion (C') of the colon (C) from an upper portion (UC) of the colon (C) as described above with reference to FIG. 7. However, instead of using an endocutter stapler (1000) to separate a lower region of the diseased portion (C') of the colon (C) from the lower portion (LC) of the colon (C) as described above with reference to FIG. 7, the operator may simply use a conventional cutting instrument (e.g., shears, knife, etc.) to cut the diseased portion (C') of the colon (C) from the lower portion (LC) of the colon (C), just above the bunched-up region of the colon (C).

The operator may then insert anvil (400) into the upper portion (UC) of the colon (C) as described above with reference to FIG. 8; and insert stapling head assembly (300) into the lower portion (LC) of the colon (C) as also described above with reference to FIG. 8. Trocar (330) may be advanced to a position where trocar (330) passes through the bunched-up region of the colon (C) and protrudes from the severed end of the lower portion (LC) of the colon (C). The operator may then secure anvil (400) to trocar (330) and clamp the adjacent regions of tissue as described above with reference to FIG. 9. It should be understood that the reduced diameter (d) of the bunched-up region of the colon (C) is smaller than the diameter (b) of knife member (340), such that the bunched-up tissue containing pleats (650) and wire (660) will fit within the cylindrical plane defined by knife member (340) at this stage. Thus, when the operator actuates stapling head assembly (330), the process will result in an anastomosis that is substantially identical to the anastomosis (A) shown in FIG. 13C, without any outwardly protruding flap regions (FR).

In some variations, wire (660) is omitted. In some such versions, receiving end (602) includes a pawl feature and pulling end (604) includes a set of integral teeth. The pawl of receiving end (602) ratchets along the integral teeth of pulling end (604) as pleating member (600) is cinched around the colon (C). The pawl and teeth thus cooperate to hold pleating member (600) in a cinched configuration, thereby holding the lower colon portion (LC) in the bunched-up, pleated (650) configuration. The cinched pleating member (600) may still be within the cylindrical plane defined by knife member (340), such that pleating member (600) is severed away with the adjacent tissue when stapling head assembly (330) is actuated to create the anastomosis (A). As yet another merely illustrative example, a suture and needle may be used in place of wire (660). Still other variations will be apparent to those of ordinary skill in the art in view of the teachings herein.

C. Exemplary Interior Pleating Member with Needle and Suture Guide

Figure 17:
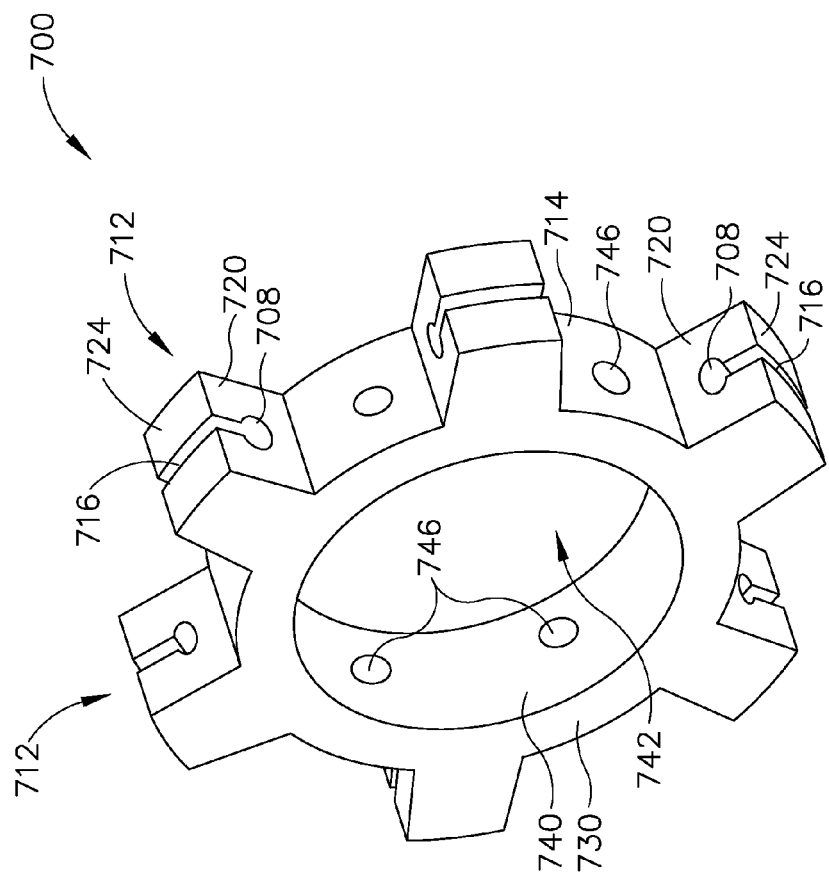
FIG. 17 depicts a perspective view of an intraluminal pleating member.
Figure 18:
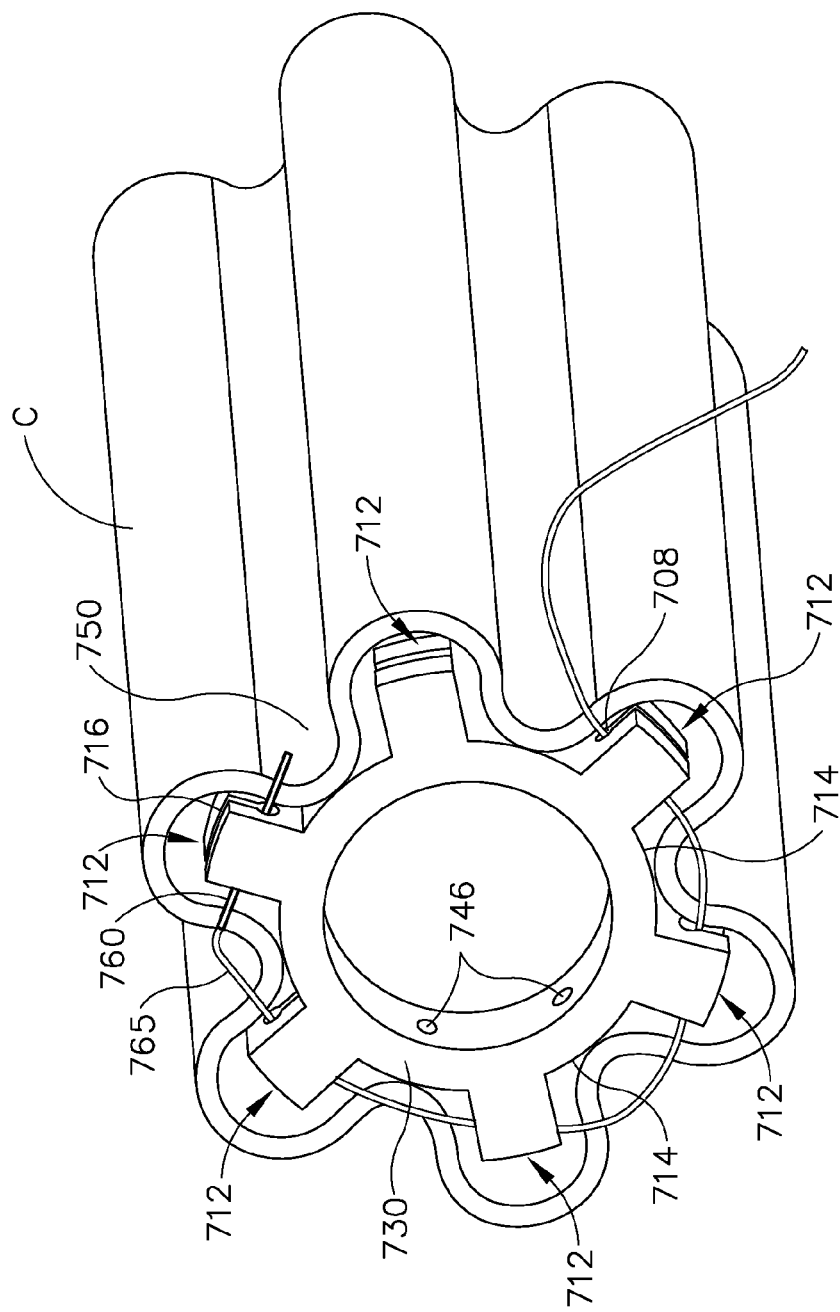
FIG. 18 depicts a perspective view of the intraluminal pleating member of FIG. 17 inserted into a recently transected gastrointestinal tract of a patient, with a needle and suture being passed through a guide path defined by the intraluminal pleating member.

FIGS. 17-18 show another exemplary pleating member (700) that may be used to form pleats (750) in a colon (C). Unlike pleating member (600) described above, pleating member (700) of this example is positioned inside a bodily lumen such as the colon (C) in order to form pleats (750) in the bodily lumen. Also unlike pleating member (600) described above, pleating member (700) of this example is configured to guide a needle (760) and suture (765) along an arcuate path. As described in greater detail below, pleating member (600), needle (760), and suture (765) are operable to form and maintain pleats (750) in a bunched-up region of the colon (C) prior to transection of the colon (C).

As seen in FIGS. 17-18, intraluminal pleating member (700) includes a body (730) having an annular inner surface (740) and an annular outer surface (714), and a plurality of protrusions (712) extending radially outwardly from annular outer surface (714). Protrusions (712) are equidistantly spaced angularly about the circumference of body (730). Annular inner surface (740) defines a central bore (742) while a plurality of radial bores (746) extend outwardly from annular inner surface (740) to annular outer surface (714). As will be described below, radial bores (746) allow for intraluminal pleating member (700) to form pleats in the colon (C). In the current example, there are four radial bores (746). However, any suitable number of radial bores (746) may be used as will be apparent to a person having ordinary skill in the art in view of the teachings herein.

Each radially extending protrusion (712) includes a pair of side faces (720), an outer face (724) connecting each pair of side faces (720), a guide channel (708) extending to each side face (720) in the pair of side faces (720), and suture exit channel (716) extending from guide channel (708) to outer face (724). Each guide channel (708) circumferentially aligns with the other wire guide channels (708) in the plurality of radially extending protrusions (712) to define an arcuate path for a needle (760) and a suture (765). While in the current example, suture exit channel (716) is shown extending from guide channel (708) to outer face (724), suture exit channel (716) may also extend from guide channel (708) to a side face (720).

As shown in FIG. 18, intraluminal pleating member (700) may be placed in the lower portion (LC) of colon (C) transanally and positioned adjacent to the location of a first desired transection (e.g., between a diseased portion (C') of the colon (C) and the patient's rectum (R)). A vacuum source (not shown) is driven to communicate with central bore (742), and the region of colon (C) above the location of pleating member (700) is temporarily crimped (e.g., using graspers, a clip, etc.). The vacuum is communicated through radial bores (746) and thereby draws the tissue of colon (C) inwardly toward annular outer surface (714). Protrusions (712) are rigid and thus bear outwardly on the tissue of colon (C), such that protrusions (712) cooperate with the suction provided through radial bores (746) to form pleats (750) in the colon (C). The resulting bunched-up region of the colon (C) has a diameter that is smaller than the diameter (b) of knife member (340). Thus, the bunched-up tissue containing pleats (750) will fit within the cylindrical plane defined by knife member (340).

While a vacuum is used to draw the tissue of the colon (C) inwardly toward pleating member (700) in this example, it should be understood that any other suitable devices or techniques may be used to draw the tissue of the colon (C) inwardly toward pleating member (700). By way of example only, a device having a complementary shape with respect to intraluminal pleating member (700) could be placed on the outside of colon (C) to press tissue into intraluminal pleating member (700). The complementary shaped device could be resiliently biased to engage intraluminal pleating member (700) and have similar wire guide channels and suture exits. Other variations will be apparent to those of ordinary skill in the art in view of the teachings herein.

With the colon (C) having the pleats (750) formed by pleating member (700), and with pleating member (700) still positioned in the colon (C), needle (760) and suture (765) may be administered from the outside of colon (C) through guide channels (708) along the arcuate path. Once needle (760) and suture (765) have traversed each guide channel (708) or each radially extending protrusion (712), the vacuum source or other device forcing colon (C) to take the shape of intraluminal pleating member (700) may be removed. Intraluminal pleating member (700) may then be removed from colon (C) transanally, with suture (765) remaining within colon (C) due to the presence of suture exits (716). In other words, as intraluminal pleating member (700) is removed from colon (C), suture (765) decouples from intraluminal pleating member (700) via suture exits (716). With pleating member (700) removed, suture (765) remains in place to hold the tissue of the colon (C) in the bunched-up configuration, maintaining the presence of pleats (750).

In an exemplary use, pleating member (700) is used to bunch-up, pleat, and guide needle (760) and suture (765) in a lower portion (LC) of the colon (C) that is between a diseased portion (C') of the colon (C) and the patient's rectum (R). The operator may then use an endocutter stapler (1000) to separate an upper region of the diseased portion (C') of the colon (C) from an upper portion (UC) of the colon (C) as described above with reference to FIG. 7. However, instead of using an endocutter stapler (1000) to separate a lower region of the diseased portion (C') of the colon (C) from the lower portion (LC) of the colon (C) as described above with reference to FIG. 7, the operator may simply use a conventional cutting instrument (e.g., shears, knife, etc.) to cut the diseased portion (C') of the colon (C) from the lower portion (LC) of the colon (C), just above the bunched-up region of the colon (C).

The operator may then insert anvil (400) into the upper portion (UC) of the colon (C) as described above with reference to FIG. 8; and insert stapling head assembly (300) into the lower portion (LC) of the colon (C) as also described above with reference to FIG. 8. Trocar (330) may be advanced to a position where trocar (330) passes through the bunched-up region of the colon (C) and protrudes from the severed end of the lower portion (LC) of the colon (C). The operator may then secure anvil (400) to trocar (330) and clamp the adjacent regions of tissue as described above with reference to FIG. 9. It should be understood that the reduced diameter (d) of the bunched-up region of the colon (C) is smaller than the diameter (b) of knife member (340), such that the bunched-up tissue containing pleats (750) and suture (765) will fit within the cylindrical plane defined by knife member (340) at this stage. Thus, when the operator actuates stapling head assembly (330), the process will result in an anastomosis that is substantially identical to the anastomosis (A) shown in FIG. 13C, without any outwardly protruding flap regions (FR).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising a staple cartridge, wherein the staple cartridge comprises: (i) a plurality of staples, (ii) a deck, wherein the deck defines a plurality of openings, wherein each opening of the plurality of openings is associated with a corresponding staple of the plurality of staples, such that each staple is configured to pass through a corresponding opening of the plurality of openings, and (iii) a buttress attached to the staple deck, wherein the buttress is configured to detach from the staple deck in response to the staples being driven through the corresponding openings of the deck, wherein the buttress is resiliently biased to transition from a first configuration while attached to the deck to a second configuration when detached from the deck, wherein the buttress has a first length in the first configuration, wherein the buttress has a second length in the second configuration, wherein the first length is longer than the second length.

Example 2

The apparatus of Example 1, wherein the buttress is substantially linear in the first configuration.

Example 3

The apparatus of Example 2, wherein the buttress is substantially linear in the second configuration.

Example 4

The apparatus of any one or more of Examples 1 through 3, wherein the buttress is resiliently biased to contract to the second length.

Example 5

The apparatus of Example 4, wherein the buttress extends longitudinally along a longitudinal axis, where wherein the buttress is resiliently biased to contract along the longitudinal axis to the second length.

Example 6

The apparatus of any one or more of Examples 4 through 3, wherein the buttress comprises an elastic material.

Example 7

The apparatus of any one or more of Examples 1 through 6, wherein the plurality of staples are configured to attach to the buttress in response to the staples being driven through the corresponding openings of the deck.

Example 8

The apparatus of Example 7, wherein the plurality of staples are configured to move toward each other in response to the buttress transitioning from the first configuration to the second configuration.

Example 9

The apparatus of any one or more of Examples 1 through 8, wherein the buttress is configured to form an arch in the second configuration.

Example 10

The apparatus of any one or more of Examples 1 through 9, wherein the buttress is configured to form a wave in the second configuration.

Example 11

The apparatus of any one or more of Examples 1 through 10, further comprising a circular stapler, wherein the circular stapler comprises: (i) an anvil, and (ii) a stapling head assembly, wherein the stapling head assembly comprises: (A) a rod configured to engage the anvil, wherein the rod is configured to pass through tissue with the staples and the buttress secured to the tissue, (B) a knife member configured to form a circular cut line in tissue, and (C) staple driver, wherein the anvil and stapling head assembly are configured to cooperate to clamp and staple tissue.

Example 12

The apparatus of Example 11, wherein the knife member defines a diameter, wherein the second length is less than the diameter of the knife member.

Example 13

The apparatus of Example 12, wherein the first length is greater than the diameter of the knife member.

Example 14

The apparatus of any one or more of Examples 1 through 13, wherein the buttress is adhered to the deck by an adhesive material.

Example 15

The apparatus of any one or more of Examples 1 through 14, wherein the deck further defines a longitudinally extending channel, wherein the openings comprise a first pair of parallel longitudinally extending arrays of openings and a second pair of parallel longitudinally extending arrays of openings, wherein the first pair is positioned on one side of the channel and the second pair is positioned on the other side of the channel, wherein the buttress extends over the first and second pairs of longitudinally extending arrays of openings.

Example 16

An apparatus comprising: (a) a body comprising: (i) a first end, (ii) a second end, wherein the second end comprises a slot, and (iii) a bendable portion configured to allow the first end to loop around and enter the slot of the second end; and (b) a plurality of protrusions extending transversely from the body, wherein the protrusions are configured to extend inwardly in response to the first end loop entering the slot of the second end, wherein each protrusion defines a respective guide channel, wherein the channels are configured to cooperate to define an arcuate passageway in response to the first end loop entering the slot of the second end, wherein the arcuate passageway is configured to guide a tissue securing member along an arc to pierce tissue manipulated by the plurality of segments.

Example 17

The apparatus of Example 16, wherein each protrusion further defines an exit channel, wherein each exit channel is in communication with the guide channel of the corresponding protrusion, wherein the exit channel is configured to allow a tissue securing member to exit the guide channel along a path that is transverse to the body.

Example 18

A method of operating on a patient, the method comprising: (a) positioning a guide body in relation to a colon of a patient, wherein the guide body includes an angularly spaced array of protrusions, wherein the protrusions form pleats in the colon, wherein the protrusions define guide passageways, wherein the guide passageways cooperate to form an arcuate path; and (b) passing a tissue securing member along the arcuate path through tissue forming the colon, wherein the act of passing the tissue securing member along the arcuate path through tissue forming the colon comprises passing the tissue securing member through the pleats.

Example 19

The method of Example 19, wherein the act of positioning the guide body in relation to a colon of a patient comprises: (i) wrapping the guide body about an exterior surface of the colon, and (ii) cinching the guide body to bear inwardly on the exterior surface of the colon to thereby reduce an effective outer diameter of the colon.

Example 20

The method of Example 19, wherein the act of positioning the guide body in relation to a colon of a patient comprises: (i) positioning the guide body in an interior region of the colon, and (ii) drawing the colon against the guide body to thereby reduce an effective outer diameter of the colon.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising a staple cartridge, wherein the staple cartridge comprises:
   (i) a plurality of staples,
   (ii) a deck, wherein the deck defines a plurality of openings, wherein each opening of the plurality of openings is associated with a corresponding staple of the plurality of staples, such that each staple is configured to pass through a corresponding opening of the plurality of openings, and
   (iii) a buttress formed from an elastic material, wherein the buttress is configured to detach from the deck in response to the staples being driven through the corresponding openings of the deck, wherein the buttress is resiliently biased to transition from a first configuration while attached to the deck to a second configuration when detached from the deck, wherein the buttress is planar and is adhered to the deck using an adhesive material in the first configuration, wherein the buttress has a maximum width that is less than a minimum width of the deck in the first configuration, wherein the buttress has a first length in the first configuration, wherein the buttress has a second length in the second configuration, wherein the first length is longer than the second length.

2. The apparatus of claim 1, wherein the buttress is substantially linear in the first configuration.

3. The apparatus of claim 2, wherein the buttress is substantially linear in the second configuration.

4. The apparatus of claim 1, wherein the buttress is resiliently biased to contract to the second length.

5. The apparatus of claim 4, wherein the buttress extends longitudinally along a longitudinal axis, wherein the buttress is resiliently biased to contract along the longitudinal axis to the second length.

6. The apparatus of claim 1, wherein the plurality of staples are configured to attach to the buttress in response to the staples being driven through the corresponding openings of the deck.

7. The apparatus of claim 6, wherein the plurality of staples are configured to move toward each other in response to the buttress transitioning from the first configuration to the second configuration.

8. The apparatus of claim 1, wherein the buttress is configured to form an arch in the second configuration.

9. The apparatus of claim 1, wherein the buttress is configured to form a wave in the second configuration.

10. The apparatus of claim 1, wherein the deck further defines a longitudinally extending channel, wherein the openings comprise a first pair of parallel longitudinally extending arrays of openings and a second pair of parallel longitudinally extending arrays of openings, wherein the first pair is positioned on one side of the channel and the second pair is positioned on the other side of the channel, wherein the buttress extends over the first and second pairs of longitudinally extending arrays of openings.

11. The apparatus of claim 1, wherein in the second configuration the buttress is configured to be secured to tissue by the plurality of staples immediately after the buttress is detached from the deck and before the buttress has time to contract to a natural position having a natural length that is less than the first and second lengths.

12. The apparatus of claim 1, wherein the buttress is configured to form a coil in the second configuration.

13. The apparatus of claim 1, wherein the plurality of staples includes at least a first staple line and a second staple line, wherein in the second configuration the first and second staple lines are attached to the buttress, wherein a distance from each staple in the first and second staple lines in the first configuration is greater than a distance from each staple in the first and second staple lines in the second configuration.

14. An apparatus comprising a staple cartridge, wherein the staple cartridge comprises:
   (i) a plurality of staples,
   (ii) a deck, wherein the deck defines a plurality of openings, wherein each opening of the plurality of openings is associated with a corresponding staple of the plurality of staples, such that each staple is configured to pass through a corresponding opening of the plurality of openings, and
   (iii) a buttress configured to detach from the staple deck in response to the staples being driven through the corresponding openings of the deck, wherein the buttress is resiliently biased to transition from a first configuration while attached to the deck to a second configuration when the buttress is attached to tissue, wherein the buttress has a first length in the first configuration, wherein the buttress has a second length in the second configuration, wherein the first length is longer than the second length, wherein the buttress is configured to form an arch in the second configuration.

15. The apparatus of claim 14, wherein the plurality of staples includes at least a first staple line and a second staple line, wherein in the second configuration the first and second staple lines are attached to the buttress, wherein a distance from each staple in the first and second staple lines in the first configuration is greater than a distance from each staple in the first and second staple lines in the second configuration.

16. An apparatus comprising a staple cartridge, wherein the staple cartridge comprises:
   (i) a plurality of staples,
   (ii) a deck, wherein the deck defines a plurality of openings, wherein each opening of the plurality of openings is associated with a corresponding staple of the plurality of staples, such that each staple is configured to pass through a corresponding opening of the plurality of openings, and
   (iii) a buttress that includes first and second opposing ends, wherein the buttress is configured to detach from the deck in response to the staples being driven through the corresponding openings of the deck, wherein the buttress is resiliently biased to transition from a first configuration while attached to the deck to a second configuration when detached from the deck, wherein the first and second opposing ends of the buttress are configured to contract toward each other in a linear fashion in the second configuration, wherein the buttress has a first length in the first configuration, wherein the buttress has a second length in the second configuration, wherein the first length is longer than the second length,
   wherein in the first configuration the buttress is planar and is adhered to the deck using an adhesive material, wherein in the first configuration the buttress has a maximum width that is less than a minimum width of the deck, wherein the plurality of staples includes at least a first staple line and a second staple line, wherein in the second configuration the first and second staple lines are attached to the buttress, wherein a distance from each staple in the first and second staple lines in the first configuration is greater than a distance from each staple in the first and second staple lines in the second configuration.

17. The apparatus of claim 16, wherein the buttress is linear in the first and second configurations.

\* \* \* \* \*